United States Patent
Zhukovsky et al.

(10) Patent No.: US 11,505,616 B2
(45) Date of Patent: *Nov. 22, 2022

(54) BINDING MOLECULES TO CD38 AND PD-L1

(71) Applicant: BIOMUNEX PHARMACEUTICALS, Paris (FR)

(72) Inventors: Eugene Zhukovsky, Bethel, CT (US); Olivier Leger, Saint Sixt (FR); Richard J. Morse, Bethel, CT (US)

(73) Assignee: BIOMUNEX PHARMACEUTICALS, Paris (FR)

( * ) Notice: Subject to any disclaimer, the term of this patent is extended or adjusted under 35 U.S.C. 154(b) by 218 days.

This patent is subject to a terminal disclaimer.

(21) Appl. No.: 16/088,181

(22) PCT Filed: Mar. 27, 2017

(86) PCT No.: PCT/EP2017/057220
§ 371 (c)(1),
(2) Date: Sep. 25, 2018

(87) PCT Pub. No.: WO2017/162890
PCT Pub. Date: Sep. 28, 2017

(65) Prior Publication Data
US 2020/0010559 A1    Jan. 9, 2020

(30) Foreign Application Priority Data

Mar. 25, 2016 (EP) .................................. 16305350

(51) Int. Cl.
C07K 16/28 (2006.01)

(52) U.S. Cl.
CPC ...... *C07K 16/2896* (2013.01); *C07K 16/2827* (2013.01); *C07K 2317/31* (2013.01); *C07K 2317/732* (2013.01); *C07K 2317/734* (2013.01); *C07K 2317/92* (2013.01)

(58) Field of Classification Search
CPC ............ C07K 16/2896; C07K 16/2827; C07K 2317/31; C07K 2317/732; C07K 2317/734; C07K 2317/92
See application file for complete search history.

(56) References Cited

U.S. PATENT DOCUMENTS

| | | | |
|---|---|---|---|
| 9,631,031 B2 | 4/2017 | Kadouche et al. | |
| 10,633,456 B1 | 4/2020 | Boyd-Kirkup et al. | |
| 10,662,241 B1 | 5/2020 | Boyd-Kirkup et al. | |
| 10,815,310 B2 | 10/2020 | Kadouche et al. | |
| 11,046,776 B2 | 6/2021 | Lazar et al. | |
| 2002/0004587 A1* | 1/2002 | Miller | A61K 47/6879 530/388.8 |
| 2014/0113348 A1 | 4/2014 | Williams et al. | |
| 2018/0057598 A1 | 3/2018 | Lazar et al. | |
| 2019/0153104 A1 | 5/2019 | Zhukovsky et al. | |
| 2019/0300610 A1 | 10/2019 | Boyd-Kirkup et al. | |
| 2019/0300624 A1 | 10/2019 | Boyd-Kirkup et al. | |
| 2019/0330377 A1 | 10/2019 | Zhukovsky et al. | |
| 2020/0283524 A1 | 9/2020 | Xu et al. | |
| 2020/0299413 A1* | 9/2020 | Zhukovsky | C12N 15/63 |
| 2020/0308275 A1 | 10/2020 | Boyd-Kirkup et al. | |
| 2020/0308308 A1 | 10/2020 | Boyd-Kirkup et al. | |
| 2021/0024651 A1 | 1/2021 | Boyd-Kirkup et al. | |
| 2021/0155712 A1 | 5/2021 | Boyd-Kirkup et al. | |

FOREIGN PATENT DOCUMENTS

| | | |
|---|---|---|
| CA | 2 929 256 | 5/2015 |
| JP | 2014-522644 | 9/2014 |
| JP | 2016-509014 | 3/2016 |
| WO | WO 2012/088461 | 6/2012 |
| WO | WO 2012/131555 | 10/2012 |
| WO | WO 2013/005194 | 1/2013 |
| WO | WO 2014/028776 | 2/2014 |
| WO | WO 2014/124326 | 8/2014 |
| WO | WO 2015/149077 | 10/2015 |
| WO | WO 2015/173756 | 11/2015 |
| WO | WO 2016/014974 | 1/2016 |
| WO | WO 2016/172485 | 10/2016 |
| WO | WO 2017/186950 | 11/2017 |
| WO | WO 2018/127608 | 7/2018 |
| WO | WO 2018/178101 | 10/2018 |

OTHER PUBLICATIONS

Lloyd et al, Protein Engineering Design & Selection (2009) 22:159-168. (Year: 2009).*
Edwards et al, J Mol Biol (2003) 14;334(1):103-118. (Year: 2003).*
Goel et al., The Journal of Immunology (2004) 173(12):7358-7367. (Year: 2004).*
Malia et al., Proteins (2016) 84;427-434 (Year: 2016).*
Barthelemy et al., Journal of Biological Chemistry, 2008, 283:3639-3654. (Year: 2008).*
Beiboer et al., Journal of Molecular Biology, 2000, 296:833-849. (Year: 2000).*
Choi et al., 2011, Molecular BioSystems, 2011,7:3327-334. (Year: 2011).*
De Genst et al., Developmental and Comparative Immunology, 2006, 30:187-98. (Year: 2006).*
Griffiths et al., The EMBO Journal, 1993, 12:725-734. (Year: 1993).*
Klimka et al., British Journal of Cancer, 2000, 83:252-260. (Year: 2000).*
Ward et al., Nature, 1989, 341:544-546. (Year: 1989).*
Holm et al., Mol. Immunol. Feb. 2007; 44 (6): 1075-1084 (Year: 2007).*
Rudikoff et al., Proc. Natl. Acad. Sci. USA 1982 vol. 79: pp. 1979-1983 (Year: 1982).*
MacCallum et al., J. Mol. Biol. Oct. 11, 1996; 262 (5): 732-745. (Year: 1996).*

(Continued)

*Primary Examiner* — Jessica H Roark
*Assistant Examiner* — Cheom-Gil Cheong
(74) *Attorney, Agent, or Firm* — Saliwanchik, Lloyd & Eisenschenk

(57) ABSTRACT

The present invention relates to a bispecific molecule comprising at least one anti-CD38 domain and at leak one anti-PD-L1 domain, which are capable of simultaneous binding to CD38 and PD-L1 antigens, respectively.

7 Claims, 7 Drawing Sheets

Specification includes a Sequence Listing.

(56) References Cited

OTHER PUBLICATIONS

Genmab, "Genmab Announces Studies of Daratumumab in Combination with Atezolizumab in a Solid Tumor and Multiple Myeloma" Company Announcement No. 15, Mar. 21, 2016, retrieved from the Internet on Jun. 1, 2017: URL:https://www.clinicalleader.com/doc/genmab-announces-studies-of-daratumumab-in-combination-with-atezolizumab-0001, pp. 1-2.

Moore, G. L. et al. "1798 Tuning T Cell Affinity Improves Efficacy and Safety of Anti-CD38 x Anti-CD3 Bispecific Antibodies in Monkeys—a Potential Therapy for Multiple Myeloma" presented Dec. 5, 2015, 57th Annual Meeting & Exposition, Orlando, Florida, pp. 1-3, retrieved from Internet on Jun. 1, 2017: URL:https://ash.confex.com/ash/2015/webprogramscheduler/Paper78382.html.

Written Opinion in International Application No. PCT/EP2017/057220, dated Jun. 26, 2017, pp. 1-6.

Chu, S. Y. et al. "Immunotherapy with Long-Lived Anti-CD38 x Anti-CD3 Bispecific Antibodies Stimulates Potent T Cell-Mediated Killing of Human Myeloma Cell Lines and CD38+ Cells in Monkeys: A Potential Therapy for Multiple Myeloma" 2014, p. 1.

Golay, J. et al. "Design and Validation of a Novel Generic Platform for the Production of Tetravalent IgG1-like Bispecific Antibodies" *The Journal of Immunology*, Apr. 1, 2016, pp. 3199-3211, vol. 196, No. 7, supplemental p. 1.

Written Opinion in International Application No. PCT/EP2018/050481, dated Mar. 26, 2018, pp. 1-10.

Chen, X. et al. "Fusion Protein Linkers: Property, Design and Functionality" *Adv Drug Deliv Rev.*, Oct. 15, 2013, vol. 65, No. 10, pp. 1357-1369.

Reusch, U. et al. "A tetravalent bispecific TandAb (CD19/CD3), AFM 11, efficiently recruits T cells for the potent lysis of CD19+ tumor cells" *MAbs*, May-Jun. 2015, vol. 7, No. 3, pp. 584-604.

Genmab Press Release, "Genmab Announces Studies of Daratumumab in Combination with Atezolizumab in a Solid Tumor and Multiple Myeloma" Mar. 21, 2016, pp. 1-2, retrieved from Internet: http://files.shareholder.com/downloads/AMDA-KPIBN/0x0x882184/5D77EB62-231D-41DA-9416-39D816CF878C/15_-Dara%20atezolizumab%20combo_210316_uk.pdf.

Mazor, Y. et al. "Enhanced tumor-targeting selectivity by modulating bispecific antibody binding affinity and format valence" *Scientific Reports*, Jan. 9, 2017, pp. 1-11, vol. 7.

Written Opinion in International Application No. PCT/EP2018/057819, dated Jul. 24, 2018, pp. 1-11.

Debiec, K. T. et al. "Evaluating the Strength of Salt Bridges: A Comparison of Current Biomolecular Force Fields" *J. Phys. Chem. B.*, 2014, pp. 6561-6569, vol. 118.

Meuzelaar, H. et al. "Influence of Glu/Arg, Asp/Arg, and Glu/Lys Salt Bridges on α-Helical Stability and Folding Kinetics" *Biophysical Journal*, Jul. 7, 2016, vol. 110, pp. 2328-2341.

Hu, S. et al., "Four-in-One Antibodies Have Superior Cancer Inhibitory Activity against EGFR, HER2, HER3, and VEGF through Disruption of HER/MET Crosstalk" *Cancer Res.*, 75(1):1-14; Jan. 1, 2015; Published Online First Nov. 4, 2014.

Moore, G. L. et al., "1798 Tuning T Cell Affinity Improves Efficacy and Safety of Anti-CD38xAnti-CD3 Bispecific Antibodies in Monkeys—a Potential Therapy for Multiple Myeloma" presented Dec. 5, 2015, 57th Annual Meeting & Exposition, Orlando, Florida, pp. 1-3).

Written Opinion in International Application No. PCT/EP2017/060280, dated Jul. 4, 2017, pp. 1-8.

Assenat, E. et al. "Dual targeting of HER1/EGFR and HER2 with cetuximab and trastuzumab in patients with metastatic pancreatic cancer after gemcitabine failure: results of the "THERAPY" phase 1-2 trial" *Oncotarget*, Feb. 28, 2015, pp. 12796-12808, vol. 6, No. 14.

Wu, X. et al. "Fab-based bispecific antibody formats with robust biophysical properties and biological activity" *mAbs*, May/Jun. 2015, pp. 470-482, vol. 7, Issue 3.

Worn, A. et al. "Stability Engineering of Antibody Single-chain Fv Fragments" *J. Mol. Biol.*, 2001, vol. 305, pp. 989-1010.

Wang, S. et al. "Effective suppression of breast tumor growth by an anti-EGFR/ErbB2 bispecific antibody" *Cancer Letters*, 2012, vol. 325, pp. 214-219.

https://clinicaltrials.gov/ct2/show/NCT00551421 pp. 1-12 (Aug. 11, 2021).

Biotechnology, Chemical, Pharmaceutical (BCP) Partnership Meeting (SPE Dan Kolker, Sep. 17, 2020; pp. 1-36).

Brinkmann, U. et al. "The making of bispecific antibodies" MABS, 2017, vol. 9, No. 2, pp. 182-212.

* cited by examiner

SDS-PAGE under reducing conditions

SDS-PAGE under non-reducing conditions

Binding ELISA

SEQUENCE LISTING

```
<160> NUMBER OF SEQ ID NOS: 32

<210> SEQ ID NO 1
<211> LENGTH: 709
<212> TYPE: PRT
<213> ORGANISM: Artificial Sequence
<220> FEATURE:
<223> OTHER INFORMATION: BiXAb 4218 heavy chain
```

```
<400> SEQUENCE: 1

Glu Val Gln Leu Leu Glu Ser Gly Gly Gly Leu Val Gln Pro Gly Gly
  1               5                  10                  15

Ser Leu Arg Leu Ser Cys Ala Val Ser Gly Phe Thr Phe Asn Ser Phe
             20                  25                  30

Ala Met Ser Trp Val Arg Gln Ala Pro Gly Lys Gly Leu Glu Trp Val
         35                  40                  45

Ser Ala Ile Ser Gly Ser Gly Gly Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Phe Cys
                 85                  90                  95

Ala Lys Asp Lys Ile Leu Trp Phe Gly Glu Pro Val Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Lys
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Thr Pro Pro Thr Pro Ser Pro Ser Gly Gly Glu Asn
                245                 250                 255

Leu Tyr Phe Gln Gly Glu Val Gln Leu Val Glu Ser Gly Gly Gly Leu
            260                 265                 270

Val Gln Pro Gly Gly Ser Leu Arg Leu Ser Cys Ala Ala Ser Gly Phe
        275                 280                 285

Thr Phe Ser Asp Ser Trp Ile His Trp Val Arg Gln Ala Pro Gly Lys
    290                 295                 300

Gly Leu Glu Trp Val Ala Trp Ile Ser Pro Tyr Gly Gly Ser Thr Tyr
305                 310                 315                 320

Tyr Ala Asp Ser Val Lys Gly Arg Phe Thr Ile Ser Ala Asp Thr Ser
                325                 330                 335

Lys Asn Thr Ala Tyr Leu Gln Met Asn Ser Leu Arg Ala Glu Asp Thr
            340                 345                 350

Ala Val Tyr Tyr Cys Ala Arg Arg His Trp Pro Gly Gly Phe Asp Tyr
        355                 360                 365

Trp Gly Gln Gly Thr Leu Val Thr Val Ser Ser Ala Ser Thr Lys Gly
    370                 375                 380

Pro Ser Val Phe Pro Leu Ala Pro Ser Ser Lys Ser Thr Ser Gly Gly
385                 390                 395                 400

Thr Ala Ala Leu Gly Cys Leu Val Lys Asp Tyr Phe Pro Glu Pro Val
                405                 410                 415
```

```
Thr Val Ser Trp Asn Ser Gly Ala Leu Thr Ser Gly Val His Thr Phe
                420                 425                 430

Pro Ala Val Leu Gln Ser Ser Gly Leu Tyr Ser Leu Ser Ser Val Val
            435                 440                 445

Glu Val Pro Ser Ser Ser Leu Gly Thr Gln Thr Tyr Ile Cys Asn Val
450                 455                 460

Asn His Lys Pro Ser Asn Thr Lys Val Asp Lys Lys Val Glu Pro Lys
465                 470                 475                 480

Ser Cys Asp Lys Thr His Thr Cys Pro Pro Cys Pro Ala Pro Glu Leu
                485                 490                 495

Leu Gly Gly Pro Ser Val Phe Leu Phe Pro Pro Lys Pro Lys Asp Thr
            500                 505                 510

Leu Met Ile Ser Arg Thr Pro Glu Val Thr Cys Val Val Val Asp Val
        515                 520                 525

Ser His Glu Asp Pro Glu Val Lys Phe Asn Trp Tyr Val Asp Gly Val
530                 535                 540

Glu Val His Asn Ala Lys Thr Lys Pro Arg Glu Glu Gln Tyr Asn Ser
545                 550                 555                 560

Thr Tyr Arg Val Val Ser Val Leu Thr Val Leu His Gln Asp Trp Leu
                565                 570                 575

Asn Gly Lys Glu Tyr Lys Cys Lys Val Ser Asn Lys Ala Leu Pro Ala
            580                 585                 590

Pro Ile Glu Lys Thr Ile Ser Lys Ala Lys Gly Gln Pro Arg Glu Pro
        595                 600                 605

Gln Val Tyr Thr Leu Pro Pro Ser Arg Glu Glu Met Thr Lys Asn Gln
610                 615                 620

Val Ser Leu Thr Cys Leu Val Lys Gly Phe Tyr Pro Ser Asp Ile Ala
625                 630                 635                 640

Val Glu Trp Glu Ser Asn Gly Gln Pro Glu Asn Asn Tyr Lys Thr Thr
                645                 650                 655

Pro Pro Val Leu Asp Ser Asp Gly Ser Phe Phe Leu Tyr Ser Lys Leu
            660                 665                 670

Thr Val Asp Lys Ser Arg Trp Gln Gln Gly Asn Val Phe Ser Cys Ser
        675                 680                 685

Val Met His Glu Ala Leu His Asn His Tyr Thr Gln Lys Ser Leu Ser
    690                 695                 700

Leu Ser Pro Gly Lys
705

<210> SEQ ID NO 2
<211> LENGTH: 214
<212> TYPE: PRT
<213> ORGANISM: Artificial Sequence
<220> FEATURE:
<223> OTHER INFORMATION: LC1

<400> SEQUENCE: 2

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60
```

```
Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Pro
                 85                  90                  95

Thr Phe Gly Gln Gly Thr Lys Val Glu Ile Lys Arg Thr Val Ala Ala
            100                 105                 110

Pro Ala Val Phe Ile Phe Pro Pro Ser Asp Glu Gln Leu Lys Ser Gly
            115                 120                 125

Thr Ala Ser Val Val Cys Leu Leu Glu Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210
```

<210> SEQ ID NO 3
<211> LENGTH: 214
<212> TYPE: PRT
<213> ORGANISM: Artificial Sequence
<220> FEATURE:
<223> OTHER INFORMATION: LC2

<400> SEQUENCE: 3

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Asp Val Ser Thr Ala
                 20                  25                  30

Val Ala Trp Tyr Gln Gln Lys Pro Gly Lys Ala Pro Lys Leu Leu Ile
             35                  40                  45

Tyr Ser Ala Ser Phe Leu Tyr Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Leu Tyr His Pro Ala
                 85                  90                  95

Thr Phe Gly Gln Gly Thr Lys Val Glu Ile Lys Arg Thr Val Ala Ala
            100                 105                 110

Pro Ala Val Phe Ile Phe Pro Pro Ser Asp Glu Gln Leu Lys Ser Gly
            115                 120                 125

Thr Ala Ser Val Val Cys Leu Leu Lys Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205
```

Phe Asn Arg Gly Glu Cys
    210

<210> SEQ ID NO 4
<211> LENGTH: 709
<212> TYPE: PRT
<213> ORGANISM: Artificial Sequence
<220> FEATURE:
<223> OTHER INFORMATION: BiXAb 4219 Heavy chain

<400> SEQUENCE: 4

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Glu Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Thr Pro Pro Thr Pro Ser Pro Ser Gly Gly Glu Asn Leu Tyr Phe Gln
                245                 250                 255

Gly Glu Val Gln Leu Leu Glu Ser Gly Gly Gly Leu Val Gln Pro Gly
            260                 265                 270

Gly Ser Leu Arg Leu Ser Cys Ala Val Ser Gly Phe Thr Phe Asn Ser
        275                 280                 285

Phe Ala Met Ser Trp Val Arg Gln Ala Pro Gly Lys Gly Leu Glu Trp
    290                 295                 300

Val Ser Ala Ile Ser Gly Ser Gly Gly Thr Tyr Tyr Ala Asp Ser Val
305                 310                 315                 320

Val Lys Gly Arg Phe Thr Ile Ser Arg Asp Asn Ser Lys Asn Thr Leu
                325                 330                 335

Tyr Leu Gln Met Asn Ser Leu Arg Ala Glu Asp Thr Ala Val Tyr Phe
            340                 345                 350

```
Cys Ala Lys Asp Lys Ile Leu Trp Phe Gly Glu Pro Val Phe Asp Tyr
        355                 360                 365

Trp Gly Gln Gly Thr Leu Val Thr Val Ser Ser Ala Ser Thr Lys Gly
    370                 375                 380

Pro Ser Val Phe Pro Leu Ala Pro Ser Ser Lys Ser Thr Ser Gly Gly
385                 390                 395                 400

Thr Ala Ala Leu Gly Cys Leu Val Lys Asp Tyr Phe Pro Glu Pro Val
                405                 410                 415

Thr Val Ser Trp Asn Ser Gly Ala Leu Thr Ser Gly Val His Thr Phe
                420                 425                 430

Pro Ala Val Leu Gln Ser Ser Gly Leu Tyr Ser Leu Ser Ser Val Val
                435                 440                 445

Lys Val Pro Ser Ser Ser Leu Gly Thr Gln Thr Tyr Ile Cys Asn Val
            450                 455                 460

Asn His Lys Pro Ser Asn Thr Lys Val Asp Lys Lys Val Glu Pro Lys
465                 470                 475                 480

Ser Cys Asp Lys Thr His Thr Cys Pro Pro Cys Pro Ala Pro Glu Leu
                485                 490                 495

Leu Gly Gly Pro Ser Val Phe Leu Phe Pro Pro Lys Pro Lys Asp Thr
                500                 505                 510

Leu Met Ile Ser Arg Thr Pro Glu Val Thr Cys Val Val Val Asp Val
            515                 520                 525

Ser His Glu Asp Pro Glu Val Lys Phe Asn Trp Tyr Val Asp Gly Val
        530                 535                 540

Glu Val His Asn Ala Lys Thr Lys Pro Arg Glu Glu Gln Tyr Asn Ser
545                 550                 555                 560

Thr Tyr Arg Val Val Ser Val Leu Thr Val Leu His Gln Asp Trp Leu
                565                 570                 575

Asn Gly Lys Glu Tyr Lys Cys Lys Val Ser Asn Lys Ala Leu Pro Ala
                580                 585                 590

Pro Ile Glu Lys Thr Ile Ser Lys Ala Lys Gly Gln Pro Arg Glu Pro
            595                 600                 605

Gln Val Tyr Thr Leu Pro Pro Ser Arg Glu Glu Met Thr Lys Asn Gln
        610                 615                 620

Val Ser Leu Thr Cys Leu Val Lys Gly Phe Tyr Pro Ser Asp Ile Ala
625                 630                 635                 640

Val Glu Trp Glu Ser Asn Gly Gln Pro Glu Asn Asn Tyr Lys Thr Thr
                645                 650                 655

Pro Pro Val Leu Asp Ser Asp Gly Ser Phe Phe Leu Tyr Ser Lys Leu
                660                 665                 670

Thr Val Asp Lys Ser Arg Trp Gln Gln Gly Asn Val Phe Ser Cys Ser
            675                 680                 685

Val Met His Glu Ala Leu His Asn His Tyr Thr Gln Lys Ser Leu Ser
        690                 695                 700

Leu Ser Pro Gly Lys
705

<210> SEQ ID NO 5
<211> LENGTH: 214
<212> TYPE: PRT
<213> ORGANISM: Artificial Sequence
<220> FEATURE:
<223> OTHER INFORMATION: LC1

<400> SEQUENCE: 5
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg Thr Val Ala Ala
            100                 105                 110

Pro Ala Val Phe Ile Phe Pro Pro Ser Asp Glu Gln Leu Lys Ser Gly
        115                 120                 125

Thr Ala Ser Val Val Cys Leu Leu Lys Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 6
<211> LENGTH: 214
<212> TYPE: PRT
<213> ORGANISM: Artificial Sequence
<220> FEATURE:
<223> OTHER INFORMATION: LC2

<400> SEQUENCE: 6

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Thr Phe Gly Gln Gly Thr Lys Val Glu Ile Lys Arg Thr Val Ala Ala
            100                 105                 110

Pro Ala Val Phe Ile Phe Pro Pro Ser Asp Glu Gln Leu Lys Ser Gly
        115                 120                 125

Thr Ala Ser Val Val Cys Leu Leu Glu Asn Phe Tyr Pro Arg Glu Ala
130                 135                 140

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
    195                 200                 205

Phe Asn Arg Gly Glu Cys
    210

<210> SEQ ID NO 7
<211> LENGTH: 710
<212> TYPE: PRT
<213> ORGANISM: Artificial Sequence
<220> FEATURE:
<223> OTHER INFORMATION: BiXAb 5104 Heavy chain

<400> SEQUENCE: 7

Gln Val Gln Leu Val Gln Ser Gly Ala Glu Val Ala Lys Pro Gly Thr
1               5                   10                  15

Ser Val Lys Leu Ser Cys Lys Ala Ser Gly Tyr Thr Phe Thr Asp Tyr
            20                  25                  30

Trp Met Gln Trp Val Lys Gln Arg Pro Gly Gln Gly Leu Glu Trp Ile
        35                  40                  45

Gly Thr Ile Tyr Gly Pro Asp Gly Asp Thr Gly Tyr Ala Gln Lys Phe
    50                  55                  60

Gln Gly Lys Ala Thr Leu Thr Ala Asp Lys Ser Ser Lys Thr Val Tyr
65                  70                  75                  80

Met His Leu Ser Ser Leu Ala Ser Glu Asp Ser Ala Val Tyr Tyr Cys
                85                  90                  95

Ala Arg Gly Asp Tyr Tyr Gly Ser Asn Ser Leu Asp Tyr Trp Gly Gln
            100                 105                 110

Gly Thr Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Lys Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Thr Pro Pro Thr Pro Ser Pro Ser Gly Gly Glu Asn Leu Tyr
                245                 250                 255

Phe Gln Gly Glu Val Gln Leu Val Glu Ser Gly Gly Gly Leu Val Gln
            260                 265                 270

Pro Gly Gly Ser Leu Arg Leu Ser Cys Ala Ala Ser Gly Phe Thr Phe
        275                 280                 285
```

```
Ser Arg Tyr Trp Met Ser Trp Val Arg Gln Ala Pro Gly Lys Gly Leu
    290                 295                 300
Glu Trp Val Ala Asn Ile Lys Gln Asp Gly Ser Glu Lys Tyr Tyr Val
305                 310                 315                 320
Asp Ser Val Lys Gly Arg Phe Thr Ile Ser Arg Asp Asn Ala Lys Asn
                325                 330                 335
Ser Leu Tyr Leu Gln Met Asn Ser Leu Arg Ala Glu Asp Thr Ala Val
            340                 345                 350
Tyr Tyr Cys Ala Arg Glu Gly Gly Trp Phe Gly Glu Leu Ala Phe Asp
        355                 360                 365
Tyr Trp Gly Gln Gly Thr Leu Val Thr Val Ser Ala Ser Thr Lys
370                 375                 380
Gly Pro Ser Val Phe Pro Leu Ala Pro Ser Ser Lys Ser Thr Ser Gly
385                 390                 395                 400
Gly Thr Ala Ala Leu Gly Cys Leu Val Lys Asp Tyr Phe Pro Glu Pro
                405                 410                 415
Val Thr Val Ser Trp Asn Ser Gly Ala Leu Thr Ser Gly Val His Thr
            420                 425                 430
Phe Pro Ala Val Leu Gln Ser Ser Gly Leu Tyr Ser Leu Ser Ser Val
        435                 440                 445
Val Glu Val Pro Ser Ser Leu Gly Thr Gln Thr Tyr Ile Cys Asn
450                 455                 460
Val Asn His Lys Pro Ser Asn Thr Lys Val Asp Lys Lys Val Glu Pro
465                 470                 475                 480
Lys Ser Cys Asp Lys Thr His Thr Cys Pro Pro Cys Pro Ala Pro Glu
                485                 490                 495
Leu Leu Gly Gly Pro Ser Val Phe Leu Phe Pro Pro Lys Pro Lys Asp
            500                 505                 510
Thr Leu Met Ile Ser Arg Thr Pro Glu Val Thr Cys Val Val Val Asp
        515                 520                 525
Val Ser His Glu Asp Pro Glu Val Lys Phe Asn Trp Tyr Val Asp Gly
530                 535                 540
Val Glu Val His Asn Ala Lys Thr Lys Pro Arg Glu Glu Gln Tyr Asn
545                 550                 555                 560
Ser Thr Tyr Arg Val Val Ser Val Leu Thr Val Leu His Gln Asp Trp
                565                 570                 575
Leu Asn Gly Lys Glu Tyr Lys Cys Lys Val Ser Asn Lys Ala Leu Pro
            580                 585                 590
Ala Pro Ile Glu Lys Thr Ile Ser Lys Ala Lys Gly Gln Pro Arg Glu
        595                 600                 605
Pro Gln Val Tyr Thr Leu Pro Pro Ser Arg Glu Glu Met Thr Lys Asn
610                 615                 620
Gln Val Ser Leu Thr Cys Leu Val Lys Gly Phe Tyr Pro Ser Asp Ile
625                 630                 635                 640
Ala Val Glu Trp Glu Ser Asn Gly Gln Pro Glu Asn Asn Tyr Lys Thr
                645                 650                 655
Thr Pro Pro Val Leu Asp Ser Asp Gly Ser Phe Phe Leu Tyr Ser Lys
            660                 665                 670
Leu Thr Val Asp Lys Ser Arg Trp Gln Gln Gly Asn Val Phe Ser Cys
        675                 680                 685
Ser Val Met His Glu Ala Leu His Asn His Tyr Thr Gln Lys Ser Leu
690                 695                 700
```

-continued

Ser Leu Ser Pro Gly Lys
705                 710

<210> SEQ ID NO 8
<211> LENGTH: 214
<212> TYPE: PRT
<213> ORGANISM: Artificial Sequence
<220> FEATURE:
<223> OTHER INFORMATION: LC1

<400> SEQUENCE: 8

Asp Ile Val Met Thr Gln Ser His Leu Ser Met Ser Thr Ser Leu Gly
1               5                   10                  15

Asp Pro Val Ser Ile Thr Cys Lys Ala Ser Gln Asp Val Ser Thr Val
            20                  25                  30

Val Ala Trp Tyr Gln Gln Lys Pro Gly Gln Ser Pro Arg Arg Leu Ile
        35                  40                  45

Tyr Ser Ala Ser Tyr Arg Tyr Ile Gly Val Pro Asp Arg Phe Thr Gly
    50                  55                  60

Ser Gly Ala Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Pro Pro Tyr
                85                  90                  95

Thr Phe Gly Gly Gly Thr Lys Leu Glu Ile Lys Arg Thr Val Ala Ala
            100                 105                 110

Pro Ala Val Phe Ile Phe Pro Pro Ser Asp Glu Gln Leu Lys Ser Gly
        115                 120                 125

Thr Ala Ser Val Val Cys Leu Leu Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 9
<211> LENGTH: 215
<212> TYPE: PRT
<213> ORGANISM: Artificial Sequence
<220> FEATURE:
<223> OTHER INFORMATION: LC2

<400> SEQUENCE: 9

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Arg Val Ser Ser Ser
            20                  25                  30

Tyr Leu Ala Trp Tyr Gln Gln Lys Pro Gly Gln Ala Pro Arg Leu Leu
        35                  40                  45

Ile Tyr Asp Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

```
Pro Glu Asp Phe Ala Val Tyr Tyr Cys Gln Gln Tyr Gly Ser Leu Pro
                85                  90                  95

Trp Thr Phe Gly Gln Gly Thr Lys Val Glu Ile Lys Arg Thr Val Ala
            100                 105                 110

Ala Pro Ala Val Phe Ile Phe Pro Pro Ser Asp Glu Gln Leu Lys Ser
        115                 120                 125

Gly Thr Ala Ser Val Val Cys Leu Leu Lys Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 10
<211> LENGTH: 702
<212> TYPE: PRT
<213> ORGANISM: Artificial Sequence
<220> FEATURE:
<223> OTHER INFORMATION: BiXAB BMX101-AP-ML1-CC1

<400> SEQUENCE: 10

Glu Val Gln Leu Leu Glu Ser Gly Gly Gly Leu Val Gln Pro Gly Gly
1               5                   10                  15

Ser Leu Arg Leu Ser Cys Ala Val Ser Gly Phe Thr Phe Asn Ser Phe
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Lys Asp Lys Ile Leu Trp Phe Gly Glu Pro Val Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Gln Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Val Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220
```

-continued

```
Cys Asp Lys Thr His Thr Ser Pro Ala Pro Ala Pro Glu Leu Leu
225                 230                 235                 240

Gly Gly Pro Ala Ala Pro Ala Pro Ala Pro Ala Gly Gly Glu Val
            245                 250                 255

Gln Leu Val Glu Ser Gly Gly Gly Leu Val Gln Pro Gly Gly Ser Leu
        260                 265                 270

Arg Leu Ser Cys Ala Ala Ser Gly Phe Thr Phe Ser Asp Ser Trp Ile
    275                 280                 285

His Trp Val Arg Gln Ala Pro Gly Lys Gly Leu Glu Trp Val Ala Trp
290                 295                 300

Ile Ser Pro Tyr Gly Gly Ser Thr Tyr Tyr Ala Asp Ser Val Lys Gly
305                 310                 315                 320

Arg Phe Thr Ile Ser Ala Asp Thr Ser Lys Asn Thr Ala Tyr Leu Gln
                325                 330                 335

Met Asn Ser Leu Arg Ala Glu Asp Thr Ala Val Tyr Tyr Cys Ala Arg
            340                 345                 350

Arg His Trp Pro Gly Gly Phe Asp Tyr Trp Gly Gln Gly Thr Leu Val
        355                 360                 365

Thr Val Ser Ser Ala Ser Thr Lys Gly Pro Ser Val Phe Pro Leu Ala
370                 375                 380

Pro Ser Ser Lys Ser Thr Ser Gly Gly Thr Ala Ala Leu Gly Cys Leu
385                 390                 395                 400

Val Lys Asp Tyr Phe Pro Glu Pro Val Thr Val Ser Trp Asn Ser Gly
                405                 410                 415

Ala Leu Thr Ser Gly Val His Thr Phe Pro Ala Val Leu Gln Ser Ser
            420                 425                 430

Gly Leu Tyr Ser Leu Ser Ser Val Val Asp Val Pro Ser Ser Ser Leu
        435                 440                 445

Gly Thr Gln Thr Tyr Ile Cys Asn Val Asn His Lys Pro Ser Asn Thr
    450                 455                 460

Lys Val Asp Lys Arg Val Glu Pro Lys Ser Cys Asp Lys Thr His Thr
465                 470                 475                 480

Cys Pro Pro Cys Pro Ala Pro Glu Leu Leu Gly Gly Pro Ser Val Phe
                485                 490                 495

Leu Phe Pro Pro Lys Pro Lys Asp Thr Leu Met Ile Ser Arg Thr Pro
            500                 505                 510

Glu Val Thr Cys Val Val Val Asp Val Ser His Glu Asp Pro Glu Val
        515                 520                 525

Lys Phe Asn Trp Tyr Val Asp Gly Val Glu Val His Asn Ala Lys Thr
    530                 535                 540

Lys Pro Arg Glu Glu Gln Tyr Asn Ser Thr Tyr Arg Val Val Ser Val
545                 550                 555                 560

Leu Thr Val Leu His Gln Asp Trp Leu Asn Gly Lys Glu Tyr Lys Cys
                565                 570                 575

Lys Val Ser Asn Lys Ala Leu Pro Ala Pro Ile Glu Lys Thr Ile Ser
            580                 585                 590

Lys Ala Lys Gly Gln Pro Arg Glu Pro Gln Val Tyr Thr Leu Pro Pro
        595                 600                 605

Ser Arg Glu Glu Met Thr Lys Asn Gln Val Ser Leu Thr Cys Leu Val
    610                 615                 620

Lys Gly Phe Tyr Pro Ser Asp Ile Ala Val Glu Trp Glu Ser Asn Gly
625                 630                 635                 640
```

-continued

```
Gln Pro Glu Asn Asn Tyr Lys Thr Thr Pro Pro Val Leu Asp Ser Asp
            645                 650                 655

Gly Ser Phe Phe Leu Tyr Ser Lys Leu Thr Val Asp Lys Ser Arg Trp
        660                 665                 670

Gln Gln Gly Asn Val Phe Ser Cys Ser Val Met His Glu Ala Leu His
    675                 680                 685

Asn His Tyr Thr Gln Lys Ser Leu Ser Leu Ser Pro Gly Lys
690                 695                 700

<210> SEQ ID NO 11
<211> LENGTH: 214
<212> TYPE: PRT
<213> ORGANISM: Artificial Sequence
<220> FEATURE:
<223> OTHER INFORMATION: Daratumumab LC

<400> SEQUENCE: 11

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Val
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 12
<211> LENGTH: 214
<212> TYPE: PRT
<213> ORGANISM: Artificial Sequence
<220> FEATURE:
<223> OTHER INFORMATION: Atezolizumab-LC

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30
```

Val Ala Trp Tyr Gln Gln Lys Pro Gly Lys Ala Pro Lys Leu Leu Ile
         35                  40                  45

Tyr Ser Ala Ser Phe Leu Tyr Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Leu Tyr His Pro Ala
                 85                  90                  95

Thr Phe Gly Gln Gly Thr Lys Val Glu Ile Lys Arg Thr Val Ala Ala
                100                 105                 110

Pro Ala Val Phe Ile Phe Pro Pro Ser Asp Glu Gln Leu Lys Ser Gly
            115                 120                 125

Thr Ala Ser Val Val Cys Leu Leu Lys Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210

<210> SEQ ID NO 13
<211> LENGTH: 34
<212> TYPE: PRT
<213> ORGANISM: Artificial Sequence
<220> FEATURE:
<223> OTHER INFORMATION: Linker 1
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (24)..(25)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be any naturally occurring amino acid
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid

<400> SEQUENCE: 13

```
Glu Pro Lys Xaa Cys Asp Lys Xaa His Xaa Xaa Pro Pro Xaa Pro Ala
1               5                   10                  15

Pro Glu Leu Leu Gly Gly Pro Xaa Xaa Pro Pro Xaa Pro Xaa Pro Xaa
            20                  25                  30

Gly Gly

<210> SEQ ID NO 14
<211> LENGTH: 34
<212> TYPE: PRT
<213> ORGANISM: Artificial Sequence
<220> FEATURE:
<223> OTHER INFORMATION: Linker 2

<400> SEQUENCE: 14

Glu Pro Lys Ser Cys Asp Lys Thr His Thr Ser Pro Pro Ala Pro Ala
1               5                   10                  15

Pro Glu Leu Leu Gly Gly Pro Gly Gly Pro Pro Gly Pro Gly Pro Gly
            20                  25                  30

Gly Gly

<210> SEQ ID NO 15
<211> LENGTH: 34
<212> TYPE: PRT
<213> ORGANISM: Artificial Sequence
<220> FEATURE:
<223> OTHER INFORMATION: Linker 2

<400> SEQUENCE: 15

Glu Pro Lys Ser Cys Asp Lys Thr His Thr Ser Pro Pro Ala Pro Ala
1               5                   10                  15

Pro Glu Leu Leu Gly Gly Pro Ala Ala Pro Pro Ala Pro Ala Pro Ala
            20                  25                  30

Gly Gly

<210> SEQ ID NO 16
<211> LENGTH: 34
<212> TYPE: PRT
<213> ORGANISM: Artificial Sequence
<220> FEATURE:
<223> OTHER INFORMATION: Linker 3

<400> SEQUENCE: 16

Glu Pro Lys Ser Cys Asp Lys Thr His Thr Ser Pro Pro Ala Pro Ala
1               5                   10                  15

Pro Glu Leu Leu Gly Gly Pro Ala Ala Pro Pro Gly Pro Ala Pro Gly
            20                  25                  30

Gly Gly

<210> SEQ ID NO 17
<211> LENGTH: 34
<212> TYPE: PRT
<213> ORGANISM: Artificial Sequence
<220> FEATURE:
<223> OTHER INFORMATION: Linker 4

<400> SEQUENCE: 17

Glu Pro Lys Ser Cys Asp Lys Thr His Thr Cys Pro Pro Cys Pro Ala
1               5                   10                  15

Pro Glu Leu Leu Gly Gly Pro Ser Thr Pro Pro Thr Pro Ser Pro Ser
            20                  25                  30

Gly Gly
```

```
<210> SEQ ID NO 18
<211> LENGTH: 34
<212> TYPE: PRT
<213> ORGANISM: Artificial Sequence
<220> FEATURE:
<223> OTHER INFORMATION: Linker 6

<400> SEQUENCE: 18

Glu Pro Lys Ser Cys Asp Lys Thr His Thr Ser Pro Pro Ser Pro Ala
1               5                   10                  15

Pro Glu Leu Leu Gly Gly Pro Ser Thr Pro Pro Thr Pro Ser Pro Ser
            20                  25                  30

Gly Gly

<210> SEQ ID NO 19
<211> LENGTH: 9
<212> TYPE: PRT
<213> ORGANISM: Artificial Sequence
<220> FEATURE:
<223> OTHER INFORMATION: Nter IgG1 CH2

<400> SEQUENCE: 19

Ala Pro Glu Leu Leu Gly Gly Pro Ser
1               5

<210> SEQ ID NO 20
<211> LENGTH: 8
<212> TYPE: PRT
<213> ORGANISM: Artificial Sequence
<220> FEATURE:
<223> OTHER INFORMATION: Portion of human IgA1 hinge

<400> SEQUENCE: 20

Thr Pro Pro Thr Pro Ser Pro Ser
1               5

<210> SEQ ID NO 21
<211> LENGTH: 19
<212> TYPE: PRT
<213> ORGANISM: Artificial Sequence
<220> FEATURE:
<223> OTHER INFORMATION: signal peptide

<400> SEQUENCE: 21

Met Asn Phe Gly Leu Arg Leu Ile Phe Leu Val Leu Thr Leu Lys Gly
1               5                   10                  15

Val Gln Cys

<210> SEQ ID NO 22
<211> LENGTH: 122
<212> TYPE: PRT
<213> ORGANISM: Homo sapiens

<400> SEQUENCE: 22

Glu Val Gln Leu Leu Glu Ser Gly Gly Gly Leu Val Gln Pro Gly Gly
1               5                   10                  15

Ser Leu Arg Leu Ser Cys Ala Val Ser Gly Phe Thr Phe Asn Ser Phe
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Thr Tyr Tyr Ala Asp Ser Val
    50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Phe Cys
                 85                  90                  95

Ala Lys Asp Lys Ile Leu Trp Phe Gly Glu Pro Val Phe Asp Tyr Trp
            100                 105                 110

Gly Gln Gly Thr Leu Val Thr Val Ser Ser
            115                 120

<210> SEQ ID NO 23
<211> LENGTH: 98
<212> TYPE: PRT
<213> ORGANISM: Artificial Sequence
<220> FEATURE:
<223> OTHER INFORMATION: CH1 domain of daratumumab

<400> SEQUENCE: 23

Ala Ser Thr Lys Gly Pro Ser Val Phe Pro Gln Ala Pro Ser Ser Lys
 1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Val Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Arg Val

<210> SEQ ID NO 24
<211> LENGTH: 118
<212> TYPE: PRT
<213> ORGANISM: Artificial Sequence
<220> FEATURE:
<223> OTHER INFORMATION: VH of atezolizumab

<400> SEQUENCE: 24

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Ser
             20                  25                  30

Trp Ile His Trp Val Arg Gln Ala Pro Gly Lys Gly Leu Glu Trp Val
         35                  40                  45

Ala Trp Ile Ser Pro Tyr Gly Gly Ser Thr Tyr Tyr Ala Asp Ser Val
     50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Arg His Trp Pro Gly Gly Phe Asp Tyr Trp Gly Gln Gly Thr
            100                 105                 110

Leu Val Thr Val Ser Ser
            115

<210> SEQ ID NO 25
```

```
<211> LENGTH: 98
<212> TYPE: PRT
<213> ORGANISM: Artificial Sequence
<220> FEATURE:
<223> OTHER INFORMATION: CH1 domain of atezolizumab

<400> SEQUENCE: 25

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Asp Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val

<210> SEQ ID NO 26
<211> LENGTH: 15
<212> TYPE: PRT
<213> ORGANISM: Homo sapiens

<400> SEQUENCE: 26

Glu Pro Lys Ser Cys Asp Lys Thr His Thr Cys Pro Pro Cys Pro
1               5                   10                  15

<210> SEQ ID NO 27
<211> LENGTH: 110
<212> TYPE: PRT
<213> ORGANISM: Homo sapiens

<400> SEQUENCE: 27

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110

<210> SEQ ID NO 28
<211> LENGTH: 107
<212> TYPE: PRT
<213> ORGANISM: Homo sapiens

<400> SEQUENCE: 28

Gly Gln Pro Arg Glu Pro Gln Val Tyr Thr Leu Pro Pro Ser Arg Glu
1               5                   10                  15
```

```
Glu Met Thr Lys Asn Gln Val Ser Leu Thr Cys Leu Val Lys Gly Phe
                20                  25                  30

Tyr Pro Ser Asp Ile Ala Val Glu Trp Glu Ser Asn Gly Gln Pro Glu
            35                  40                  45

Asn Asn Tyr Lys Thr Thr Pro Pro Val Leu Asp Ser Asp Gly Ser Phe
 50                  55                  60

Phe Leu Tyr Ser Lys Leu Thr Val Asp Lys Ser Arg Trp Gln Gln Gly
 65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
                100                 105
```

<210> SEQ ID NO 29
<211> LENGTH: 107
<212> TYPE: PRT
<213> ORGANISM: Homo sapiens

<400> SEQUENCE: 29

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Pro
                85                  90                  95

Thr Phe Gly Gln Gly Thr Lys Val Glu Ile Lys
                100                 105
```

<210> SEQ ID NO 30
<211> LENGTH: 107
<212> TYPE: PRT
<213> ORGANISM: Artificial Sequence
<220> FEATURE:
<223> OTHER INFORMATION: CKappa domain of daratumumab

<400> SEQUENCE: 30

```
Arg Thr Val Ala Ala Pro Ser Val Phe Ile Phe Pro Pro Ser Asp Glu
1               5                   10                  15

Gln Leu Lys Ser Gly Thr Ala Ser Val Thr Cys Leu Leu Asn Asn Phe
                20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
 50                  55                  60

Thr Tyr Ser Leu Val Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
                100                 105
```

```
<210> SEQ ID NO 31
<211> LENGTH: 107
<212> TYPE: PRT
<213> ORGANISM: Artificial Sequence
<220> FEATURE:
<223> OTHER INFORMATION: VL of atezolizumab

<400> SEQUENCE: 31

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys
            100                 105

<210> SEQ ID NO 32
<211> LENGTH: 107
<212> TYPE: PRT
<213> ORGANISM: Artificial Sequence
<220> FEATURE:
<223> OTHER INFORMATION: CKappa domain of atezolizumab

<400> SEQUENCE: 32

Arg Thr Val Ala Ala Pro Ala Val Phe Ile Phe Pro Pro Ser Asp Glu
1               5                   10                  15

Gln Leu Lys Ser Gly Thr Ala Ser Val Val Cys Leu Leu Lys Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

BINDING MOLECULES TO CD38 AND PD-L1

CROSS-REFERENCE TO RELATED APPLICATION

This application is the U.S. national stage application of International Patent Application No. PCT/EP2017/057220, filed Mar. 27, 2017.

The Sequence Listing for this application is labeled "Seq-List.txt" which was created on Sep. 21, 2018, and is 54 KB. The entire content of the sequence listing is incorporated herein by reference in its entirety.

The invention relates to CD38/PD-L1 binding molecules, especially antibodies, targeting CD38 and PD-L1, methods for the production of these molecules, compositions, and uses thereof.

BACKGROUND OF THE INVENTION

Multiple Myeloma (MM) is the third most common haematological malignancy with 114,000 cases globally per year. Despite advances in treatment, MM remains one of the few haematological malignancies with an unmet medical need. Once patients progress through front-line therapy and have relapsed or refractory (r/r) disease, treatment options are very limited. However, in the recent years anti-MM tumor target antigens (TAA) have been developed. One anti-CD38 antibody, daratumumab, has been approved for the treatment of patients with relapsed MM and other anti-CD38 antibodies are currently in development (isatuximab and MOR-202, which is described in U.S. Pat. No. 8,263,746). However, there is a need to improve responses that are currently in the range of 30-35%. It was demonstrated that the activity of anti-CD38 antibodies may be enhanced by immunomodulatory therapeutics (e.g. lenalidomide), which stimulate the immune system of patients. Additionally it was demonstrated that one of the mechanisms of resistance of MM tumor cells to antibody therapies is associated with the increased signalling of checkpoint inhibitor pathways (e.g. PD-1/PD-L1). Therefore, there is an opportunity to enhance cytotoxicity of anti-CD38 antibodies against MM tumor cells and simultaneously activate the immune system by inhibiting checkpoint inhibitor pathways (e.g. PD-1/PD-L1).

In physiological conditions, PD-L1 plays a major role as guard against autoimmunity by down-regulating the immune system. It is expressed on immune "APC-like" cells (T cells, NK cells, macrophages, myeloid DCs, B cells, epithelial cells, vascular endothelial cells) and tumor cells. PD-L1 binds to its cognate receptors PD-1 and B7-1, and negatively regulates immune cells (T cells, NK cells, etc.), by inhibiting their proliferation and activation.

In pathological conditions, PD-L1 is highly expressed by tumor cells (>90% MM patients) and is associated with poor prognosis. Blocking antibodies targeting immune checkpoint pathways (anti-PD-1, anti-CTLA-4, anti-PD-L1, etc.) have demonstrated remarkable activity in different types of cancer (lung, melanoma etc.). Signs of efficacy have been observed in MM, however the activity of this class of promising therapeutics is still suboptimal in MM. One of the reasons could be that molecules, which possess beneficial activity/side effect profile (e.g. anti-PD-L1) require near stoichiometric blocking/saturation of their targets to elicit maximal immunostimulatory effect on T cells.

Therefore, specific targeting of anti-PD-L1 antibodies to the site of tumors (e.g. targeting CD38+ cancer cells) may help delivering anti-PD-L1 therapeutics to the site where immune stimulation is required, and may result in maximal immune cell stimulation allowing the complete blocking of PD-L1 on tumor and microenvironment cells. Such targeted immune cell activation at tumor sites may also reduce systemic activation of the immune cells, prevent adverse side effects, and permit higher dosing of therapeutic antibodies.

SUMMARY OF THE INVENTION

To harness the cytotoxic capacity of T cells, BK cells and other immune cells for the treatment of multiple myeloma (MM) and other cancers, preferably CD38+ cancers, bispecific molecules with two binding sites (specific for CD38 and PD-L1 respectively) were designed. The bispecific molecules of the invention remove the inhibition of the immune system associated with the interaction of PD-1 on T cells and NK cells and PD-L1, expressed on tumor and tumor microenvironment cells. Such molecules are useful in treating cancers, especially multiple myeloma or any CD38+ cancers, which overexpress PD-L1, and grow in the microenvironments of PD-L1 expressing immune cells (Plasmacytoid Dendritic Cell, Myeloid-derived Suppressor Cells) that further inhibit T cells and NK cells. The molecules of the invention facilitate the Antibody-dependent cell-mediated cytotoxicity (ADCC), phagocytosis, and complement-dependent cytotoxicity (CDC) of CD38+/PD-L1+ tumor cells as well as PD-L1+ cells of tumor microenvironment cells.

In one of the embodiments of the invention, several bispecific CD38/PD-L1 molecules, comprising anti-CD38 and anti-PD-L1 domains, are engineered. These bispecific CD38/PD-L1 molecules are capable of simultaneous binding to both antigens.

More particularly, bispecific CD38/PD-L1 antibodies, comprising anti-CD38 and anti-PD-L1 domains, are engineered. These bispecific CD38/PD-L1 antibodies are capable of simultaneous binding to both antigens.

In a preferred embodiment, bispecific CD38/PD-L1 antibodies are expressed in CHO cells and are purified by affinity chromatography employing Protein A resins. Antibody binding properties are characterized in in vitro assays. They simultaneously bind both CD38 and PD-L1 in ELISA assay.

The bispecific tetravalent four Fab antibodies, having the structure of FIG. 1A or 1B are designated BiXAb®, a trademark of Biomunex Therapeutics.

The antibody of the invention is a bispecific and bivalent for CD38 and PD-L1. The antigen-binding bispecific antibodies of the invention are full-length bispecific antibodies consisting of a continuous "composite heavy chain" (made of the natural heavy chain of IgG of mAb1 followed by Linkers and the Fab heavy chain of mAb2), which is constructed of an Fc (Hinge-CH2-CH3) followed by antibody 1 Fab heavy chain (CH1-VH) and the successive Fab heavy chain (CH1-VH) of antibody 2, the latter joined by a hinge-derived polypeptide linker sequence, and the resulting composite heavy chain during protein expression, associates with the identical second composite heavy chain, while the co-expressed Fab light chains (LC) of antibody 2 and of antibody 1 associate with their cognate heavy chain domains in order to form the final tandem F(ab')$_2$-Fc molecule; the antibody 1 (Ab1) and the antibody 2 (Ab2) being different and selected from the group consisting of anti-CD38 antibodies (daratumumab, isatuximab, MOR-202 or any other anti-CD38 antibody) or their mutated derivatives and anti- PD-L1 antibodies (atezolizumab, durvalumab, avelumab, MDX-1105 or any other anti-PD-L1 antibody) or their mutated derivatives.

The BiXAb® antibodies are able to bind bivalently both to CD38 and PD-L1.

Further described is a polypeptide which consists of a heavy chain of the bispecific antibody as defined above, as well as a polynucleotide comprising a sequence encoding said polypeptide.

A host cell transfected with an expression vector comprising said polynucleotide is also described.

Still another object of the invention is a method for preparing the bispecific antibodies of the invention.

A method for producing the bispecific antibody of the invention is thus provided, said method comprising the following steps: a) culturing in suitable medium and culture conditions a host cell expressing an antibody heavy chain as defined above, and antibody light chains as defined above; and b) recovering said produced antibodies from the culture medium or from said cultured cells.

The invention makes use of recombinant vectors, in particular expression vectors, comprising polynucleotides encoding the heavy and light chains defined herein, associated with transcription- and translation-controlling elements which are active in the host cell chosen. Vectors which can be used to construct expression vectors in accordance with the invention are known in themselves, and will be chosen in particular as a function of the host cell one intends to use. Preferably, said host cell is transformed with a polynucleotide encoding a heavy chain and two polynucleotides encoding two different light chains. Said polynucleotides can be inserted in a same expression vector, or in separate expression vectors. The method for producing the antibodies of the invention comprises culturing such host-cell and recovering said antigen-binding fragments or antibody from said culture.

LEGENDS TO THE FIGURES

Figure 8A:
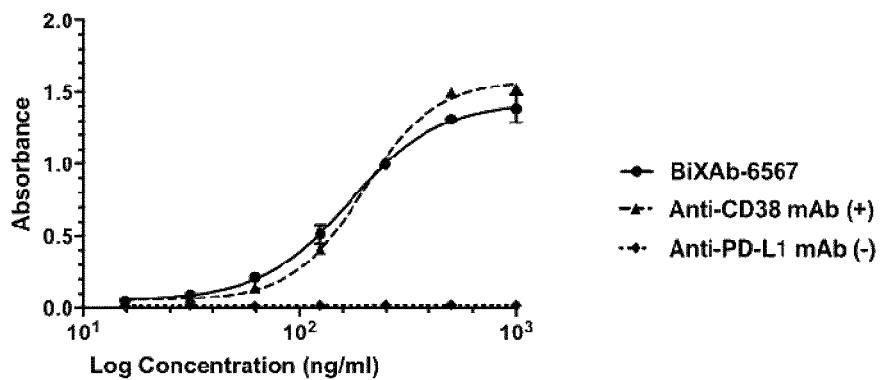
Figure 8B:
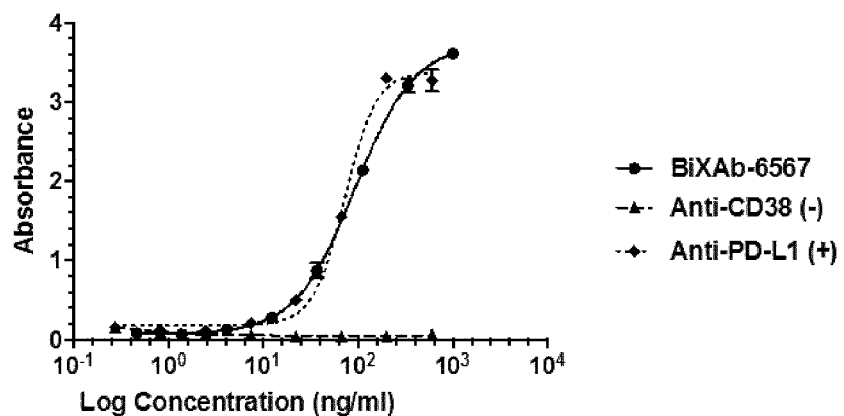
Figure 8C:
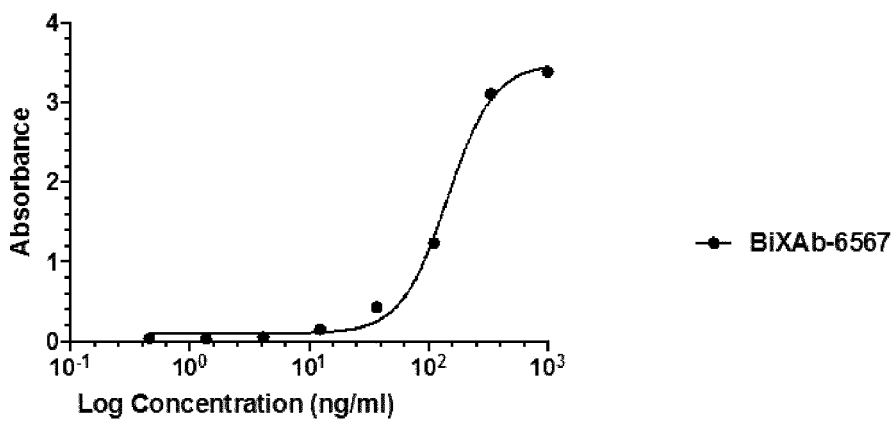

FIG. 8A shows the binding profiles of the two parental antibodies (anti-CD38 and anti-PD-L1) and BiXAb-6567 in a direct CD38 antigen binding ELISA. FIG. 8B shows the binding profiles of the two parental antibodies (anti-CD38 and anti-PD-L1) and BiXAb-6567 in a direct PD-L1 antigen binding ELISA. FIG. 8C shows the binding profile of BiXAb-6567 in a dual antigen (PD-L1 and CD38) binding ELISA.

Figure 9A:
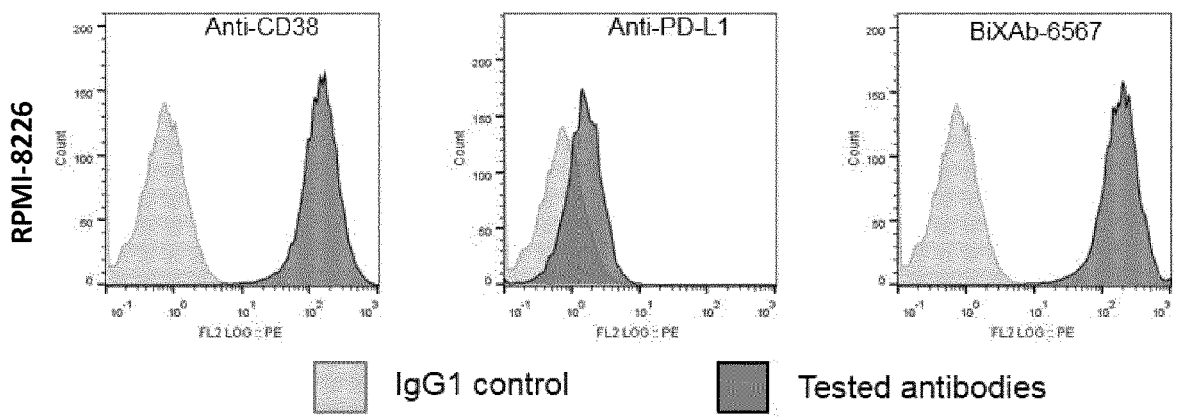
Figure 9B:
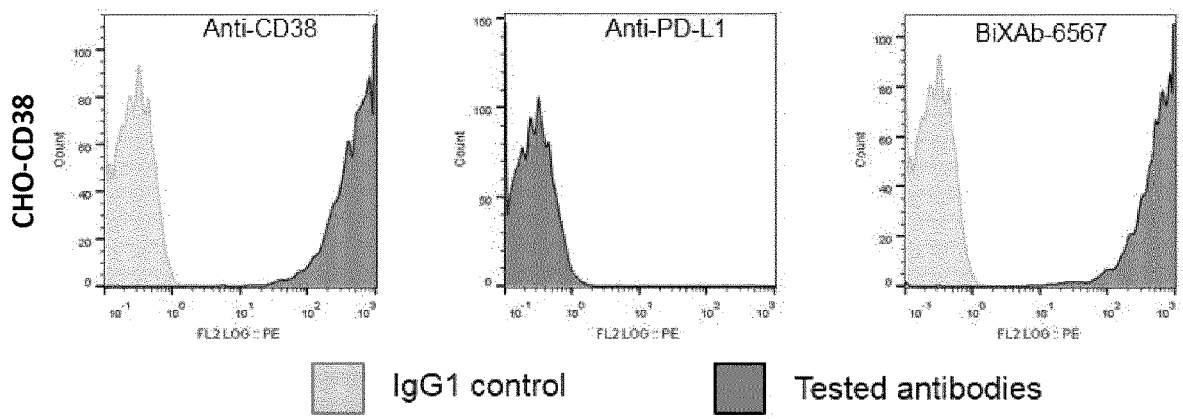
Figure 9C:
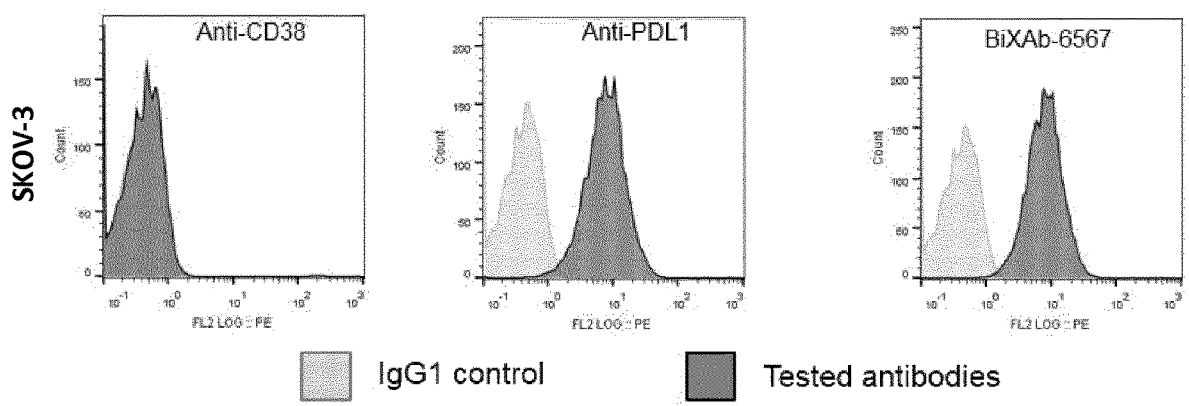

FIGS. 9A to 9C show Fluorescence-activated cell sorting profiles of the two parental mAbs (anti-CD38 and anti-PD-L1) and BiXAb-6567 on three different cell lines, 9A: multiple myeloma RPMI-8226, 9B: CHO cells stably transfected with full-length CD38, and 9C: ovarian cancer cell line SKOV-3.

Figure 10:
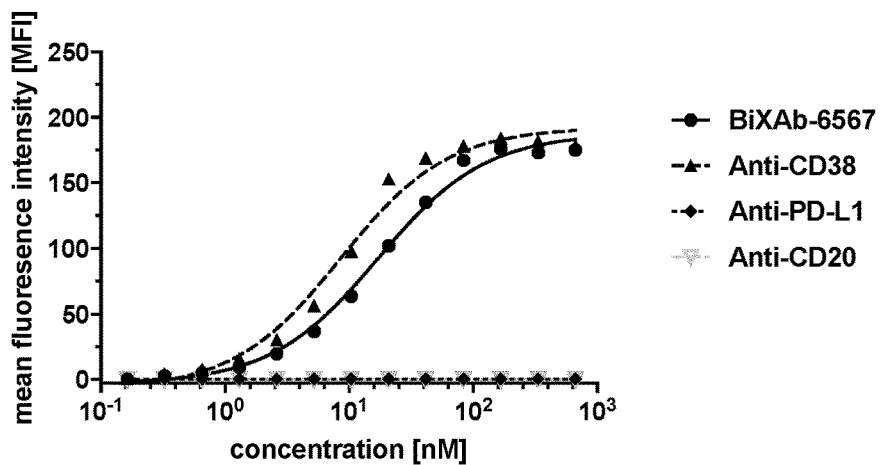

FIG. 10 shows the titration binding profiles on the CHO-CD38 cell line of the two parental antibodies (anti-CD38 and anti-PD-L1), BiXAb-6567, and the negative control anti-CD20 antibody.

Figure 11:
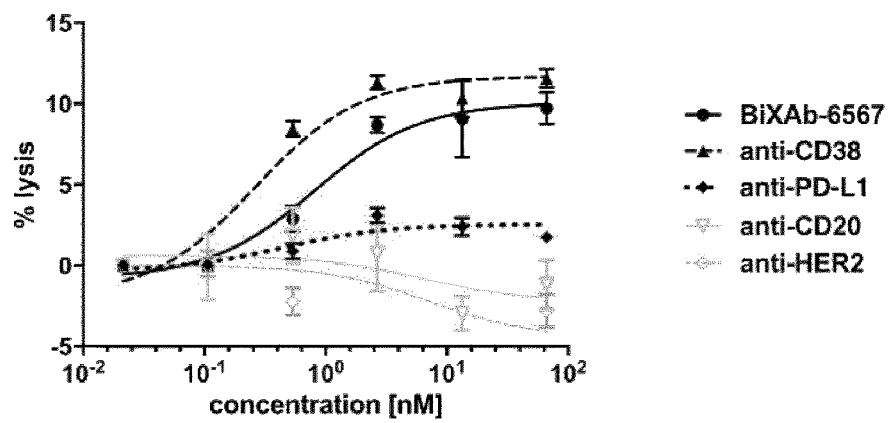

FIG. 11 shows the cytotoxic activity profiles of the two parental antibodies (anti-CD38 and anti-PD-L1), BiXAb-6567, and two negative control antibodies, anti-CD20 and anti-HER2, in an ADCC assay employing a multiple myeloma cell line, RPMI-8226, as target cells and unfractionated non-pre-activated mononuclear cells as effector cells.

Figure 12:
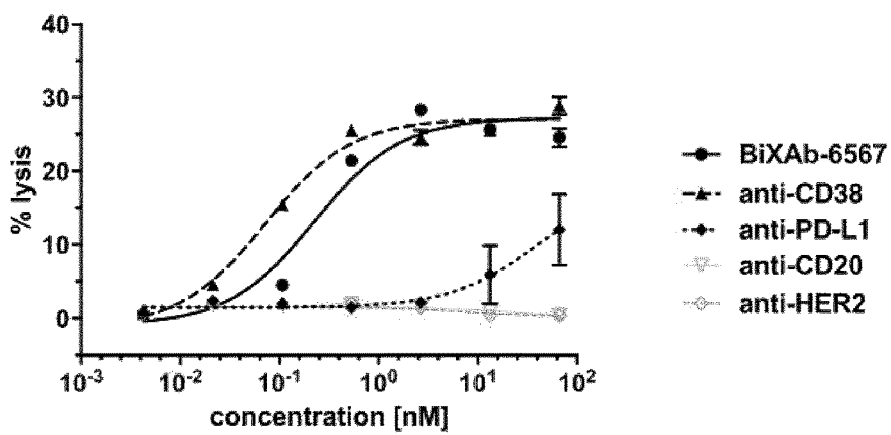

FIG. 12 shows the cytotoxic activity profiles of the two parental antibodies (anti-CD38 and anti-PD-L1), BiXAb-6567, and two negative control antibodies, anti-CD20 and anti-HER2, in an ADCC assay with the CHO-CD38 cell line as target cells and unfractionated non-pre-activated mononuclear cells as effector cells.

Figure 13:
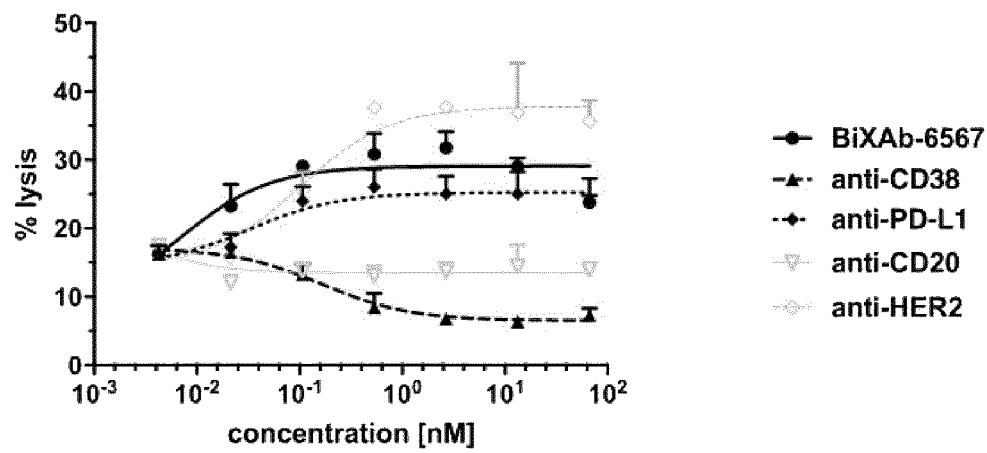

FIG. 13 shows the cytotoxic activity profiles of the two parental antibodies (anti-CD38 and anti-PD-L1), BiXAb-6567, and two negative control antibodies, anti-CD20 and anti-HER2, in an ADCC assay with the SKOV-3 cell line as target cells and enriched IL-12 pre-activated NK cells as effector cells.

Figure 14:
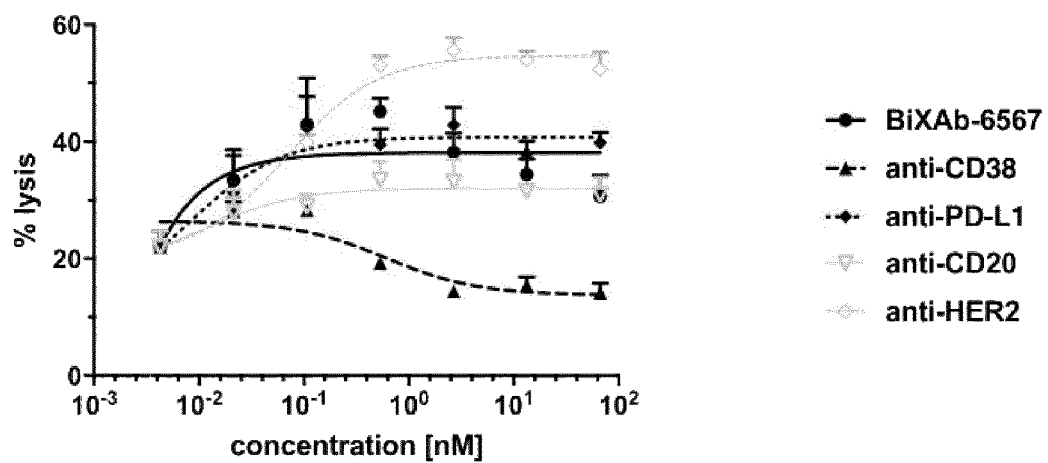

FIG. 14 shows the cytotoxic activity profiles of the two parental antibodies (anti-CD38 and anti-PD-L1), BiXAb-6567, and two negative control antibodies, anti-CD20 and anti-HER2, in an ADCC assay with the SKOV-3 cell line as target cells and enriched IL-15 pre-activated NK cells as effector cells.

DETAILED DESCRIPTION

Definitions

The basic structure of a naturally occurring antibody molecule is a Y-shaped tetrameric quaternary structure consisting of two identical heavy chains and two identical light chains, held together by non-covalent interactions and by inter-chain disulfide bonds.

In mammalian species, there are five types of heavy chains: α, δ, ε, γ, and μ, which determine the class (isotype) of immunoglobulin: IgA, IgD, IgE, IgG, and IgM, respectively. The heavy chain N-terminal variable domain (VH) is followed by a constant region, containing three domains (numbered CH1, CH2, and CH3 from the N-terminus to the C-terminus) in heavy chains γ, α, and δ, while the constant region of heavy chains μ and ε is composed of four domains (numbered CH1, CH2, CH3 and CH4 from the N-terminus to the C-terminus). The CH1 and CH2 domains of IgA, IgG, and IgD are separated by a flexible hinge, which varies in length between the different classes and in the case of IgA and IgG, between the different subtypes: IgG1, IgG2, IgG3, and IgG4 have respectively hinges of 15, 12, 62 (or 77), and 12 amino acids, and IgA1 and IgA2 have respectively hinges of 20 and 7 amino acids.

There are two types of light chains: λ and κ, which can associate with any of the heavy chains isotypes, but are both of the same type in a given antibody molecule. Both light chains appear to be functionally identical. Their N-terminal variable domain (VL) is followed by a constant region consisting of a single domain termed CL.

The heavy and light chains pair by protein/protein interactions between the CH1 and CL domains, and via VH/VL interactions and the two heavy chains associate by protein/protein interactions between their CH3 domains. The structure of the immunoglobulin molecule is generally stabilized by interchains disulfide bonds between the CH1 and CL domains and between the hinges.

The antigen-binding regions correspond to the arms of the Y-shaped structure, which consist each of the complete light chain paired with the VH and CH1 domains of the heavy chain, and are called the Fab fragments (for Fragment antigen binding). Fab fragments were first generated from native immunoglobulin molecules by papain digestion which cleaves the antibody molecule in the hinge region, on the amino-terminal side of the interchains disulfide bonds, thus releasing two identical antigen-binding arms. Other proteases such as pepsin, also cleave the antibody molecule in the hinge region, but on the carboxy-terminal side of the interchains disulfide bonds, releasing fragments consisting of two identical Fab fragments and remaining linked through disulfide bonds; reduction of disulfide bonds in the F(ab')2 fragments generates Fab' fragments.

The part of the antigen binding region corresponding to the VH and VL domains is called the Fv fragment (for Fragment variable); it contains the CDRs (complementarity determining regions), which form the antigen-binding site (also termed paratope).

The effector region of the antibody which is responsible of its binding to effector molecules or cells, corresponds to the stem of the Y-shaped structure, and contains the paired CH2 and CH3 domains of the heavy chain (or the CH2, CH3 and CH4 domains, depending on the class of antibody), and is called the Fc (for Fragment crystallisable) region.

Due to the identity of the two heavy chains and the two light chains, naturally occurring antibody molecules have two identical antigen-binding sites and thus bind simultaneously to two identical epitopes.

An antibody "specifically binds" to a target antigen if it binds with greater affinity, avidity, more readily, and/or with greater duration than it binds to other substances. "Specific binding" or "preferential binding" does not necessarily require (although it can include) exclusive binding. Generally, but not necessarily, reference to binding means preferential binding.

The terms "subject," "individual," and "patient" are used interchangeably herein and refer to a mammal being assessed for treatment and/or being treated. Subjects may be human, but also include other mammals, particularly those mammals useful as laboratory models for human disease, e.g. mouse, rat, rabbit, dog, etc.

The term "treatment" or "treating" refers to an action, application or therapy, wherein a subject, including a human being, is subjected to medical aid with the purpose of improving the subject's condition, directly or indirectly. Particularly, the term refers to reducing incidence, or alleviating symptoms, eliminating recurrence, preventing recurrence, preventing incidence, improving symptoms, improving prognosis or combination thereof in some embodiments. The skilled artisan would understand that treatment does not necessarily result in the complete absence or removal of symptoms. For example, with respect to cancer, "treatment" or "treating" may refer to slowing neoplastic or malignant cell growth, proliferation, or metastasis, preventing or delaying the development of neoplastic or malignant cell growth, proliferation, or metastasis, or some combination thereof.

Design of the Preferred Bispecific Antibodies:

The invention provides bispecific tetravalent antibodies, comprising two binding sites to each of their targets, and a functional Fc domain allowing the activation of effector functions such as antibody-dependent cell-mediated cytotoxicity (ADCC), phagocytosis, and complement-dependent cytotoxicity (CDC).

The antibodies of the invention are full-length antibodies. They preferably comprise heavy chains and light chains from human immunoglobulins, preferably IgG, still preferably IgG1.

The light chains preferably are Kappa light chains.

In a preferred embodiment, the linker of the invention connects two pairs of IgG Fab domains in a tetra-Fab bispecific antibody format, the amino acid sequence of which comprises the heavy chain sequences of at least two Fab joined by a linker, followed by the native hinge sequence, followed by the IgG Fc sequence, coexpressed with the appropriate IgG light chain sequences.

Figure 1A:
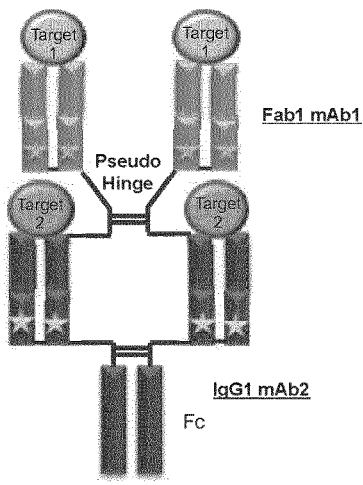
FIGS. 1A and 1B are schematic representations of a bispecific antibody of the invention, which comprises two heavy chains, and four light chains.
Figure 1B:
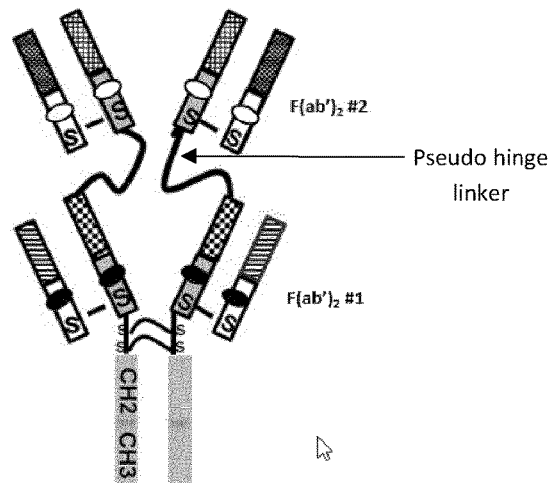

An example of the antibodies of the invention, which have an IgG-like structure, is illustrated in FIGS. 1A and 1B.

The bispecific antibodies of the invention typically comprise
 a continuous heavy chain constructed of an Fc (Hinge-CH2-CH3),
 followed by antibody 1 Fab heavy chain (CH1-VH) and the successive Fab heavy chain (CH1-VH) of antibody 2, the latter joined by a hinge-derived polypeptide linker sequence,
 and during protein expression the resulting heavy chain assembles into dimers while the co-expressed antibody 1 and antibody 2 light chains (VL-CL) associate with their cognate heavy chains in order to form the final tandem F(ab)'2-Fc molecule, the antibody 1 (Ab1) and the antibody 2 (Ab2) being different.

Ab1 and Ab2, being different, independently are selected from the group consisting of an anti-CD38 antibody (such as daratumumab) and an anti-PD-L1 antibody (such as atezolizumab).

Daratumumab binds a unique CD38 epitope at the C-terminal region of human CD38, amino acids 233 to 246 and 267 to 280, with amino acids in positions 272 and 274 being particularly important for binding. Advantageously, Ab1 and/or Ab2 may be antibodies that bind to the same epitope, or overlapping epitope (e.g. with an overlap of at least 4 amino acids) with respect to daratumumab.

In another embodiment, Ab1 and/or Ab2 may be antibodies that bind to the same epitope, or overlapping epitope with respect to atezolizumab.

In a particular embodiment, the bispecific molecule is a bispecific antibody which comprises, preferably consists of, a) two heavy chains, each comprising, preferably consisting of, SEQ ID NO:1 and b) four light chains, two comprising, preferably consisting of, SEQ ID NO:2, the two others comprising, preferably consisting of, SEQ ID NO: 3. Such bispecific antibody is designated BiXAb-4218.

In another particular embodiment, the bispecific molecule is a bispecific antibody which comprises, preferably consists of, a) two heavy chains, each comprising, preferably consisting of, SEQ ID NO:4 and b) four light chains, two comprising, preferably consisting of, SEQ ID NO:5, the two others comprising, preferably consisting of, SEQ ID NO: 6. Such bispecific antibody is designated BiXAb-4219.

In another particular embodiment, the bispecific molecule is a bispecific antibody which comprises, preferably consists of, a) two heavy chains, each comprising, preferably consisting of, SEQ ID NO:7 and b) four light chains, two comprising, preferably consisting of, SEQ ID NO:8, the two others comprising, preferably consisting of, SEQ ID NO: 9. Such bispecific antibody is designated BiXAb-5104.

In a preferred embodiment, the bispecific molecule is a bispecific antibody which comprises, preferably consists of, a) two heavy chains, each comprising, preferably consisting of, SEQ ID NO:10 and b) four light chains, two comprising, preferably consisting of, SEQ ID NO:11, the two others comprising, preferably consisting of, SEQ ID NO: 12. Such bispecific antibody is designated BiXAb-6567.

The heavy chain (SEQ ID NO:10) comprises
VH of daratumumab (SEQ ID NO:22)
CH1 domain (human IgG1 of G1m(3) allotype with mutations L124Q and S188V) of daratumumab Fab (SEQ ID NO:23)
AP linker (SEQ ID NO:15)
VH of atezolizumab (SEQ ID NO: 24)
CH1 domain (human IgG1 of G1m(3) allotype with the mutation T192D) of atezolizumab Fab (SEQ ID NO:25)
Hinge of human IgG1 (SEQ ID NO:26)
CH2 domain of human IgG1 (SEQ ID NO:27)
CH3 domain of human IgG1 of G1m(3) allotype (SEQ ID NO:28).
Light chain SEQ ID NO: 11 comprises
VL of daratumumab (SEQ ID NO:29)
CKappa domain of daratumumab with mutations V133T and S176V (SEQ ID NO:30) Light chain SEQ ID NO: 12 comprises
VL of atezolizumab (SEQ ID NO: 31)
CKappa domain of atezolizumab with mutations S114A and N137K (SEQ ID NO:32).

Bispecific antibodies with improved properties are also described, which show a higher binding affinity to CD38 and/or to PD-L1. For instance, such bispecific antibodies can show a Kd less than $1\times10^{-7}$ M, $10^{-8}$ M, preferably less than $1\times10^{-9}$ or $1\times10^{-10}$ M, with respect to CD38 and/or PD-L1.

Design of the Linkers

The polypeptide linker, also designated "hinge-derived polypeptide linker sequence" or "pseudo hinge linker", comprises all or part of the sequence of the hinge region of one or more immunoglobulin(s) selected among IgA, IgG, and IgD, preferably of human origin. Said polypeptide linker may comprise all or part of the sequence of the hinge region of only one immunoglobulin. In this case, said immunoglobulin may belong to the same isotype and subclass as the immunoglobulin from which the adjacent CH1 domain is derived, or to a different isotype or subclass. Alternatively, said polypeptide linker may comprise all or part of the sequences of hinge regions of at least two immunoglobulins of different isotypes or subclasses. In this case, the N-terminal portion of the polypeptide linker, which directly follows the CH1 domain, preferably consists of all or part of the hinge region of an immunoglobulin belonging to the same isotype and subclass as the immunoglobulin from which said CH1 domain is derived.

Optionally, said polypeptide linker may further comprise a sequence of from 2 to 15, preferably of from 5 to 10 N-terminal amino acids of the CH2 domain of an immunoglobulin.

The polypeptide linker sequence typically consists of less than 80 amino acids, preferably less than 60 amino acids, still preferably less than 40 amino acids.

In some cases, sequences from native hinge regions can be used; in other cases point mutations can be brought to these sequences, in particular the replacement of one or more cysteine residues in native IgG1, IgG2 or IgG3 hinge sequences by alanine or serine, in order to avoid unwanted intra-chain or inter-chains disulfide bonds.

In a particular embodiment, the polypeptide linker sequence comprises or consists of amino acid sequence EPKX$_1$CDKX$_2$HX$_3$X$_4$PPX$_5$PAPELLGGPX$_6$X$_7$PPX$_8$PX$_9$PX$_{10}$GG (SEQ ID NO:13), wherein X$_1$, X$_2$, X$_3$, X$_4$, X$_5$, X$_6$, X$_7$, X$_8$, X$_9$, X$_{10}$, identical or different, are any amino acid. In particular, the polypeptide linker sequence may comprise or consist of a sequence selected from the group consisting of

```
                                         (SEQ ID NO: 14)
    EPKSCDKTHTSPPAPAPELLGGPGGPPGPGPGGG;

(SEQ ID NO: 15)
    EPKSCDKTHTSPPAPAPELLGGPAAPPAPAPAGG;

(SEQ ID NO: 16)
    EPKSCDKTHTSPPAPAPELLGGPAAPPGPAPGGG;

(SEQ ID NO: 17)
    EPKSCDKTHTCPPCPAPELLGGPSTPPTPSPSGG
    and (SEQ ID NO: 18)
    EPKSCDKTHTSPPSPAPELLGGPSTPPTPSPSGG.
```

A non-limitative example of a hinge-derived polypeptide linker which can be used in a multispecific antigens-binding fragment of the invention is a polypeptide having SEQ ID NO:17. Said polypeptide consists of the full length sequence of human IgG1 hinge, followed by the 9 N-terminal amino-acids of human IgG1 CH2 (APELLGGPS, SEQ ID NO: 19), by a portion of the sequence of human IgA1 hinge (TPPTPSPS, SEQ ID NO: 20), and by the dipeptide GG, added to provide supplemental flexibility to the linker. In another preferred embodiment, the hinge-derived polypeptide linker sequence is SEQ ID NO: 15 or SEQ ID NO:18.

In a particular embodiment, $X_1$, $X_2$ and $X_3$, identical or different, are Threonine (T) or Serine (S).

In another particular embodiment, $X_1$, $X_2$ and $X_3$, identical or different, are selected from the group consisting of Ala (A), Gly (G), Val (V), Asn (N), Asp (D) and Ile (I), still preferably $X_1$, $X_2$ and $X_3$, identical or different, may be Ala (A) or Gly (G).

Alternatively, $X_1$, $X_2$ and $X_3$, identical or different, may be Leu (L), Glu (E), Gln (Q), Met (M), Lys (K), Arg (R), Phe (F), Tyr (T), His (H), Trp (W), preferably Leu (L), Glu (E), or Gln (Q).

In a particular embodiment, $X_4$ and $X_5$, identical or different, are any amino acid selected from the group consisting of Serine (S), Cysteine (C), Alanine (A), and Glycine (G).

In a preferred embodiment, $X_4$ is Serine (S) or Cysteine (C).

In a preferred aspect, $X_5$ is Alanine (A) or Cysteine (C).

In a particular embodiment, $X_6$, $X_7$, $X_8$, $X_9$, $X_{10}$, identical or different, are any amino acid other than Threonine (T) or Serine (S). Preferably $X_6$, $X_7$, $X_8$, $X_9$, $X_{10}$, identical or different, are selected from the group consisting of Ala (A), Gly (G), Val (V), Asn (N), Asp (D) and Ile (I).

Alternatively, $X_6$, $X_7$, $X_8$, $X_9$, $X_{10}$, identical or different, may be Leu (L), Glu (E), Gln (Q), Met (M), Lys (K), Arg (R), Phe (F), Tyr (T), His (H), Trp (W), preferably Leu (L), Glu (E), or Gln (Q).

In a preferred embodiment, $X_6$, $X_7$, $X_8$, $X_9$, $X_{10}$, identical or different, are selected from the group consisting of Ala (A) and Gly (G).

In still a preferred embodiment, $X_6$ and $X_7$ are identical and are preferably selected from the group consisting of Ala (A) and Gly (G).

In a preferred embodiment, the polypeptide linker sequence comprises or consists of sequence SEQ ID NO: 13, wherein $X_1$, $X_2$ and $X_3$, identical or different, are Threonine (T), Serine (S);

$X_4$ is Serine (S) or Cysteine (C);

$X_5$ is Alanine (A) or Cysteine (C);

$X_6$, $X_7$, $X_8$, $X_9$, $X_{10}$, identical or different, are selected from the group consisting of Ala (A) and Gly (G).

In another preferred embodiment, the polypeptide linker sequence comprises or consists of sequence SEQ ID NO: 13, wherein $X_1$, $X_2$ and $X_3$, identical or different, are Ala (A) or Gly (G);

$X_4$ is Serine (S) or Cysteine (C);

$X_5$ is Alanine (A) or Cysteine (C);

$X_6$, $X_7$, $X_8$, $X_9$, $X_{10}$, identical or different, are selected from the group consisting of Ala (A) and Gly (G).

Production of the Bispecific Antibodies:

The skilled person may refer to international patent application WO2013/005194, herein incorporated by reference, for general techniques of expressing multispecific antibodies.

Also herein described is a polynucleotide comprising a sequence encoding a protein chain of the molecule or antibody of the invention. Said polynucleotide may also comprise additional sequences: in particular it may advantageously comprise a sequence encoding a leader sequence or signal peptide allowing secretion of said protein chain. Host-cells transformed with said polynucleotide are also disclosed.

Typically, the amino acid sequences of different anti-CD38 and anti-PDL-1 monoclonal antibodies are used to design the DNA sequences, optionally after codon optimization for mammalian expression. For the heavy chain, the DNAs encoding signal peptides, variable region and constant CH1 domain of Fab1 followed the hinge linker and variable region and constant CH1 domain of Fab2 with flanking sequences for restriction enzyme digestion are synthesized. For the light chain, the DNAs encoding signal peptides and variable and constant Kappa regions are synthesized.

Nucleic acids encoding heavy and light chains of the antibodies of the invention are inserted into expression vectors. The light and heavy chains can be cloned in the same or different expression vectors. The DNA segments encoding immunoglobulin chains are operably linked to control sequences in the expression vector(s) that ensure the expression of immunoglobulin polypeptides. Such control sequences include a signal sequence, a promoter, an enhancer, and a transcription termination sequence. Expression vectors are typically replicable in the host organisms either as episomes or as an integral part of the host chromosomal DNA. Commonly, expression vectors will contain selection markers, e.g., tetracycline or neomycin, to permit detection of those cells transformed with the desired DNA sequences.

In one example, both the heavy and light chain-coding sequences (e.g., sequences encoding a VH and a VL, a VH-CH1 and a VL-CL, or a full-length heavy chain and a full-length light chain) are included in one expression vector. In another example, each of the heavy and light chains of the antibody is cloned into an individual vector. In the latter case, the expression vectors encoding the heavy and light chains can be co-transfected into one host cell for expression of both chains, which can be assembled to form intact antibodies either in vivo or in vitro. Alternatively, the expression vector encoding the heavy chain and that or those encoding the light chains can be introduced into different host cells for expression each of the heavy and light chains, which can then be purified and assembled to form intact antibodies in vitro.

In a particular embodiment, a host cell is co-transfected with three independent expression vectors, such as plasmids, leading to the coproduction of all three chains (namely the heavy chain HC, and two light chains LC1 and LC2, respectively) and to the secretion of the bispecific antibody.

More especially the three vectors may be advantageously used in a following molecular ratio of 2:1:1 (HC:LC1:LC2).

The recombinant vectors for expression the antibodies described herein typically contain a nucleic acid encoding the antibody amino acid sequences operably linked to a promoter, either constitutive or inducible. The vectors can be suitable for replication and integration in prokaryotes, eukaryotes, or both. Typical vectors contain transcription and translation terminators, initiation sequences, and promoters useful for regulation of the expression of the nucleic acid encoding the antibody. The vectors optionally contain generic expression cassettes containing at least one independent terminator sequence, sequences permitting replication of the cassette in both eukaryotes and prokaryotes, i.e., shuttle vectors, and selection markers for both prokaryotic and eukaryotic systems.

Bispecific antibodies as described herein may be produced in prokaryotic or eukaryotic expression systems, such as bacteria, yeast, filamentous fungi, plant, insect (e.g. using a baculovirus vector), and mammalian cells. It is not necessary that the recombinant antibodies of the invention are glycosylated or expressed in eukaryotic cells; however, expression in mammalian cells is generally preferred. Examples of useful mammalian host cell lines are human embryonic kidney line (293 cells), baby hamster kidney cells (BHK cells), Chinese hamster ovary cells/− or + DHFR (CHO, CHO-S, CHO-DG44, Flp-in CHO cells), African green monkey kidney cells (VERO cells), and human liver cells (Hep G2 cells).

Mammalian tissue cell culture is preferred to express and produce the polypeptides because a number of suitable host cell lines capable of secreting intact immunoglobulins have been developed in the art, and include the CHO cell lines, various Cos cell lines, HeLa cells, preferably myeloma cell lines (such as NSO), or transformed B-cells or hybridomas.

In a most preferred embodiment, the bispecific antibodies of the invention are produced by using a CHO cell line, most advantageously CHO-S or CHO-DG-44 cell lines or their derivatives.

Expression vectors for these cells can include expression control sequences, such as an origin of replication, a promoter, and an enhancer, and necessary processing information sites, such as ribosome binding sites, RNA splice sites, polyadenylation sites, and transcriptional terminator sequences. Preferred expression control sequences are promoters derived from immunoglobulin genes, SV40, adenovirus, bovine papilloma virus, cytomegalovirus and the like.

The vectors containing the polynucleotide sequences of interest (e.g., the heavy and light chain encoding sequences and expression control sequences) can be transferred into the host cell by well-known methods, which vary depending on the type of cellular host. For example calcium phosphate treatment or electroporation may be used for other cellular hosts. (See generally Sambrook et al., Molecular Cloning: A Laboratory Manual (Cold Spring Harbor Press, 2nd ed., 1989). When heavy and light chains are cloned on separate expression vectors, the vectors are co-transfected to obtain expression and assembly of intact immunoglobulins.

Host cells are transformed or transfected with the vectors (for example, by chemical transfection or electroporation methods) and cultured in conventional nutrient media (or modified as appropriate) for inducing promoters, selecting transformants, or amplifying the genes encoding the desired sequences.

The expression of the antibodies may be transient or stable.

Preferably, the bispecific antibodies are produced by the methods of stable expression, in which cell lines stably transfected with the DNA encoding all polypeptide chains of a bispecific antibody, such as BiXAb-6567, are capable of sustained expression, which enables manufacturing of therapeutics. For instance stable expression in a CHO cell line is particularly advantageous.

Once expressed, the whole antibodies, their dimers, individual light and heavy chains, or other immunoglobulin forms of the present invention can be further isolated or purified to obtain preparations that substantially homogeneous for further assays and applications. Standard protein purification methods known in the art can be used. For example, suitable purification procedures may include fractionation on immunoaffinity or ion-exchange columns, ethanol precipitation, high-performance liquid chromatography (HPLC), sodium dodecyl sulfate polyacrylamide gel electrophoresis (SDS-PAGE), ammonium sulfate precipitation, and gel filtration (see generally Scopes, Protein Purification (Springer-Verlag, N.Y., 1982). Substantially pure immunoglobulins of at least about 90 to 95% homogeneity are preferred, and 98 to 99% or more homogeneity most preferred, for pharmaceutical uses.

In vitro production allows scale-up to give large amounts of the desired bispecific antibodies of the invention. Such methods may employ homogeneous suspension culture, e.g. in an airlift reactor or in a continuous stirrer reactor, or immobilized or entrapped cell culture, e.g. in hollow fibers, microcapsules, on agarose microbeads or ceramic cartridges.

Mutated Derivatives and Mutations:

The polypeptide sequences that bind CD38 may derive from any anti-CD38 antibody, e.g. selected from the group consisting of daratumumab, isatuximab, MOR-202 or their mutated derivatives.

The polypeptide sequences that bind PD-L1 may derive from any anti-PD-L1 antibody, e.g. selected from the group consisting atezolizumab, durvalumab, avelumab, MDX-1105 or their mutated derivatives.

The term "mutated derivative", "mutant", or "functional variant" designates a sequence that differs from the parent sequence to which it refers by deletion, substitution or insertion of one or several amino acids. Preferably the mutated derivative preferably show at least 80%, preferably at least 85%, still preferably at least 90% homology sequence with the native sequence. In a particular embodiment, the mutations do not substantially impact the function of the antibody.

Mutated derivatives, or functional variants, can comprise a VH chain that comprises an amino acid sequence at least 85% (e.g., 90%, 92%, 94%, 95%, 96%, 97%, 98%, or 99%) identical to any of the reference sequences recited herein, a VL chain that has an amino acid sequence at least 85% (e.g., 90%, 92%, 94%, 95%, 96%, 97%, 98%, or 99%) identical to any of the reference sequences recited herein, or both. These variants are capable of binding to CD38 and PD-L1. In some examples, the variants possess similar antigen-binding affinity relative to the reference antibodies described above (e.g., having a KD less than $1\times10^{-7}$M, $10^{-8}$ M, preferably less than $1\times10^{-9}$ or $1\times10^{-10}$ M).

The affinity of the binding is defined by the terms ka (associate rate constant), kd (dissociation rate constant), or KD (equilibrium dissociation). Typically, specifically binding when used with respect to an antibody refers to an antibody that specifically binds to ("recognizes") its target(s) with an affinity (KD) value less than $10^{-7}$ M, preferably less than $10^{-8}$ M, e.g., less than $10^{-9}$ M or $10^{-10}$ M. A lower KD value represents a higher binding affinity (i.e., stronger binding) so that a KD value of $10^{-9}$ indicates a higher binding affinity than a KD value of $10^{-8}$.

The "percent identity" of two amino acid sequences is determined using the algorithm of Karlin and Altschul Proc. Natl. Acad. Sci. USA 87:2264-68, 1990, modified as in Karlin and Altschul Proc. Natl. Acad. Sci. USA 90:5873-77, 1993. Such an algorithm is incorporated into the NBLAST and XBLAST programs (version 2.0) of Altschul, et al. J. Mol. Biol. 215:403-10, 1990. BLAST protein searches can be performed with the XBLAST program, score=50, word-length=3 to obtain amino acid sequences homologous to the protein molecules of interest. Where gaps exist between two sequences, Gapped BLAST can be utilized as described in Altschul et al., Nucleic Acids Res. 25(17):3389-3402, 1997. When utilizing BLAST and Gapped BLAST programs, the default parameters of the respective programs (e.g., XBLAST and NBLAST) can be used.

In other embodiments, the functional variants described herein can contain one or more mutations (e.g., conservative substitutions) which preferably do not occur at residues which are predicted to interact with one or more of the CDRs.

It is herein described mutated derivatives, or functional variants, which are substantially identical to the reference antibody.

The term "substantially identical" or "insubstantial" means that the relevant amino acid sequences (e.g., in framework regions (FRs), CDRs, VH, or VL domain) of a variant differ insubstantially (e.g., including conservative amino acid substitutions) as compared with a reference antibody such that the variant has substantially similar binding activities (e.g., affinity, specificity, or both) and bioactivities relative to the reference antibody. Such a variant may include minor amino acid changes, e.g. 1 or 2 substitutions in a 5 amino acid sequence of a specified region. Generally, more substitutions can be made in FR regions, in contrast to CDR regions, as long as they do not adversely impact the binding function of the antibody (such as reducing the binding affinity by more than 50% as compared to the original antibody). In some embodiment, the sequence identity can be about 85%, 90%, 95%, 96%, 97%, 98%, 99% or higher, between the original and the modified antibody. In some embodiments, the modified antibody has the same binding specificity and has at least 50% of the affinity of the original antibody.

Conservative substitutions will produce molecules having functional and chemical characteristics similar to those of the molecule from which such modifications are made. For example, a "conservative amino acid substitution" may involve a substitution of a native amino acid residue with another residue such that there is little or no effect on the polarity or charge of the amino acid residue at that position. Desired amino acid substitutions (whether conservative or non-conservative) can be determined by those skilled in the art. For example, amino acid substitutions can be used to identify important residues of the molecule sequence, or to increase or decrease the affinity of the molecules described herein. Variants comprising one or more conservative amino acid substitutions can be prepared according to methods for altering polypeptide sequence known to one of ordinary skill in the art such as are found in references which compile such methods, e.g. Molecular Cloning: A Laboratory Manual, J. Sambrook, et al., eds., Second Edition, Cold Spring Harbor Laboratory Press, Cold Spring Harbor, N.Y., 1989, or Current Protocols in Molecular Biology, F. M. Ausubel, et al., eds., John Wiley & Sons, Inc., New York. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

The present disclosure also provides antibody variants with improved biological properties of the antibody, such as higher or lower binding affinity, or with altered ADCC properties on CD38 and/or PD-L1 expressing cells.

Amino acid sequence variants of the antibody can be prepared by introducing appropriate nucleotide changes into the antibody nucleic acid, or via peptide synthesis. Such modifications include, for example, deletions from, and/or insertions into and/or substitutions of, residues within the amino acid sequences of the antibody. Any combination of deletion, insertion, and substitution is made to achieve the final construct, provided that the final construct possesses the desired characteristics. Nucleic acid molecules encoding amino acid sequence variants of the antibody can be prepared by a variety of methods known in the art. These methods include, but are not limited to, oligonucleotide-mediated (or site-directed) mutagenesis, PCR mutagenesis, and cassette mutagenesis of an earlier prepared variant or a non-variant (natural) version of the antibody. In one embodiment, the equilibrium dissociation constant (KD) value of the antibodies of the invention is less than $10^{-7}$ M, particularly less than $10^{-8}$ M, $10^{-9}$ M or $10^{-10}$ M. The binding affinity may be determined using techniques known in the art, such as ELISA or biospecific interaction analysis (e.g. using surface plasmon resonance), or other techniques known in the art.

Any of the molecules described herein can be examined to determine their properties, such as antigen-binding activity, antigen-binding specificity, and biological functions, following routine methods.

Any of the molecules described herein can be modified to contain additional nonproteinaceous moieties that are known in the art and readily available, e.g., by PEGylation, hyperglycosylation, and the like. Modifications that can enhance serum half-life are of interest.

Throughout the present description, amino acid sequences are defined according to Kabat et al, Sequences of Proteins of Immunological Interest, 5th Ed. Public Health Service, National Institutes of Health, Bethesda, Md. (1991).

Mutations can be located in constant domains. The bispecific antibodies indeed advantageously comprise Fab fragments having mutations at the interface of the CH1 and CL domains, said mutations facilitate cognate pairing of heavy chain/light chain and preventing their mispairing.

In a preferred embodiment, bispecific antibodies are described herein, which comprise
    two Fab fragments with different mutated CH1 and mutated CL domains consisting of
        a) Fab fragment having mutated CH1 and mutated C-Kappa domains derived from a human IgG1/Kappa, and the VH and VL domains of Ab1,
        b) Fab fragment having mutated CH1 and mutated C-Kappa domains derived from a human IgG1/Kappa and the VH and VL domains of Ab2,
        c) a mutated light chain constant domain which is derived from human Kappa constant domain,
    the Fab fragments being tandemly arranged in the following order
        the C-terminal end of the mutated CH1 domain of Ab1 Fab fragment being linked to the N-terminal end of the VH domain of Ab2 Fab fragment through a polypeptide linker,
        the hinge region of a human IgG1 linking the C-terminal end of mutated CH1 domain of Ab2 fragment to the N-terminal of the CH2 domain,
        the dimerized CH2 and CH3 domains of a human IgG1.

In particular examples, bispecific antibodies are described, wherein the Fab CH1 domain of one of Ab1 or Ab2 is a mutated domain that derives from the CH1 domain of an immunoglobulin by substitution of the threonine residue at position 192 of said CH1 domain with an aspartic acid and the cognate CL domain is a mutated domain that derives from the CL domain of an immunoglobulin by substitution of the asparagine residue at position 137 of said CL domain with a lysine residue and substitution of the serine residue at position 114 of said CL domain with an alanine residue, and/or wherein the Fab CH1 domain of one or the other of Ab1 or Ab2 is a mutated domain that derives from the CH1 domain of an immunoglobulin by substitution of the leucine residue at position 124 of said CH1 domain with a glutamine and substitution of the serine residue at position 188 of said CH1 domain with a valine residue, and the cognate CL domain is a mutated domain that derives from the CL domain of an immunoglobulin by substitution of the valine residue at position 133 of said CL domain with a threonine residue and substitution of the serine residue at position 176 of said CL domain with a valine residue.

The antibodies of the invention may be glycosylated or not, or may show a variety of glycosylation profiles. In a preferred embodiment, antibodies are unglycosylated on the variable region of the heavy chains, but are glycosylated on the Fc region.

Certain mutated derivatives may use humanized forms of the reference antibody. In a humanization approach, complementarity determining regions (CDRs) and certain other amino acids from donor mouse variable regions are grafted into human variable acceptor regions and then joined to human constant regions. See, e.g. Riechmann et al., Nature 332:323-327 (1988); U.S. Pat. No. 5,225,539.

Therapeutic Uses:

The bispecific molecule, preferably antibody, of the invention is useful as a medicament, in particular in treating a cancer.

The term "cancer" as used herein includes any cancer, especially a hematological malignancy, and any other cancer characterized by CD38 or PD-L1 expression or overexpression, and especially those cancers characterized by co-expression of both CD38 and PD-L1.

Examples of cancers are lymphoma or leukemia, such as Non-Hodgkin's lymphoma (NHL), acute lymphocytic leukemia (ALL), acute myeloid leukemia (AML), chronic lymphocytic leukemia (CLL), chronic myelogenous leukemia (CML), or multiple myeloma (MM), breast cancer, ovarian cancer, head and neck cancer, bladder cancer, melanoma, colorectal cancer, pancreatic cancer, lung cancer, leiomyoma.

It is thus described a method of treatment of a patient suffering from cancer by administering a bispecific molecule according to the invention to said patient in the need of such treatment.

Another aspect of the invention is thus the use of the bispecific molecule according to the invention for the manufacture of a medicament for the treatment of cancer.

One aspect of the invention is a pharmaceutical composition comprising a bispecific molecule according to the invention. Another aspect of the invention is the use of a bispecific molecule according to the invention for the manufacture of a pharmaceutical composition. A further aspect of the invention is a method for the manufacture of a pharmaceutical composition comprising a bispecific molecule according to the invention.

In another aspect, the present invention provides a composition, e.g. a pharmaceutical composition, containing a bispecific molecule as defined herein, formulated together with a pharmaceutical carrier.

As used herein, a "pharmaceutical carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g. by injection or infusion).

A composition of the present invention can be administered by a variety of methods known in the art. The route and/or mode of administration will vary depending upon the desired results.

To administer the bispecific molecule or antibody of the invention by certain routes of administration, it may be necessary to coat the bispecific molecule or antibody of the invention with, or co-administer the bispecific molecule or antibody of the invention with a material to prevent its inactivation. For example, the bispecific molecule or antibody of the invention may be administered to a subject in an appropriate carrier, for example, liposomes, or a diluent. Pharmaceutically acceptable diluents include saline and aqueous buffer solutions. Pharmaceutical carriers include sterile aqueous solutions or dispersions and sterile powders for the extemporaneous preparation of sterile injectable solutions or dispersion. The use of such media and agents for pharmaceutically active substances is known in the art.

These compositions may also contain adjuvants such as preservatives, wetting agents, emulsifying agents and dispersing agents. Prevention of presence of microorganisms may be ensured both by sterilization procedures and by the inclusion of various antibacterial and antifungal agents, for example, paraben, chlorobutanol, phenol, sorbic acid, and the like. It may also be desirable to include isotonic agents, such as sodium chloride into the compositions. In addition, prolonged absorption of the injectable pharmaceutical form may be brought about by the inclusion of agents, which delay absorption.

Actual dosage levels of the active ingredients in the pharmaceutical compositions of the present invention may be varied so as to obtain an amount of the active ingredient, which is effective to achieve the desired therapeutic response for a particular patient, composition, and mode of administration, without being toxic to the patient.

The selected dosage level will depend upon a variety of pharmacokinetic factors including the activity of the particular compositions of the present invention employed, the route of administration, the time of administration, the duration of the treatment, other drugs, compounds and/or materials used in combination with the particular compositions employed, the age, sex, weight, condition, general health and prior medical history of the patient being treated, and like factors well known in the medical arts. For example the bispecific molecule or antibody of the invention can be administrated at a dosage of 0.2-20 mg/kg from 3 times/week to 1 time/month.

The present invention, thus generally described above, will be understood more readily by reference to the following examples, which are provided by way of illustration and are not intended to be limiting the instant invention.

EXAMPLES

Example 1. Preparation of Bispecific Antibodies BiXAb-4218, BiXAb-4219 and BiXAb-5104

Gene Synthesis

The amino acid sequences of different anti-CD38 and anti-PDL-1 monoclonal antibodies were used to design the DNA sequences after codon optimization for mammalian expression using GeneScript program. For the heavy chain, the DNAs encoding signal peptides, variable region and constant CH1 domain of Fab1 followed the hinge linker and variable region and constant CH1 domain of Fab2 with flanking sequences for restriction enzyme digestion were synthesized by GeneScript. For the light chain, the DNAs encoding signal peptides and variable and constant Kappa regions were synthesized by GeneScript.

PCR reactions using PfuTurbo Hot Start were carried out to amplify the inserts which were then digested by NotI+ApaI and NotI+HindIII for heavy and light chains, respectively. The double digested heavy chain fragments were ligated with NotI+ApaI digested Evitria's proprietary expression vector in which the human IgG1 CH1+hinge+CH2+CH3 domains were already inserted. The double digested light chain fragments were ligated with NotI+HindIII treated Evitria's proprietary vector. Plasmid DNAs were verified by double strand DNA sequencing.

Expression, Purification and Characterization

Figure 2:
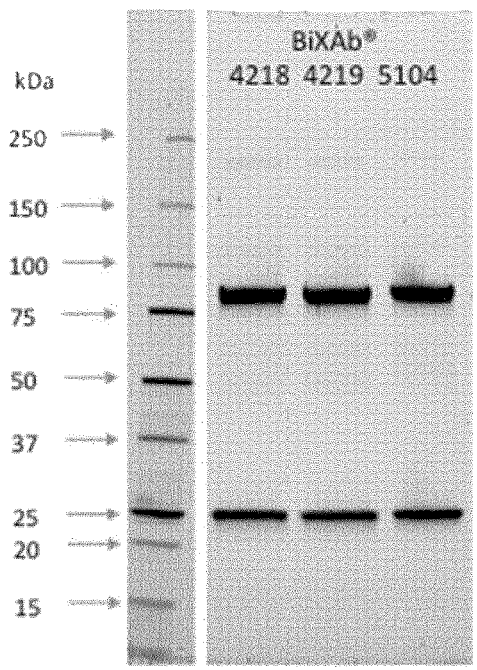
FIG. 2 shows a SDS polyacrylamide gel electrophoresis of bispecific antibodies BiXAbs 4218, 4219 and 5104 under reducing conditions.
Figure 3:
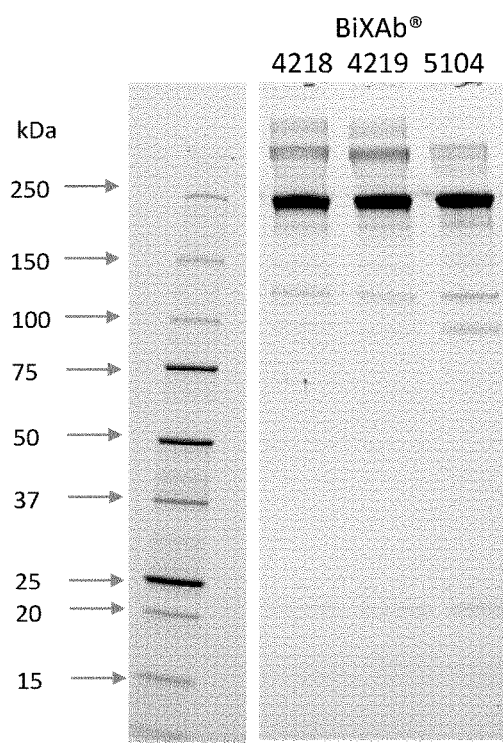
FIG. 3 shows a SDS polyacrylamide gel electrophoresis of BiXAbs 4218, 4219 and 5104 under non-reducing conditions.

For a 50 mL scale expression, a total of 50 µg of plasmid DNAs in Evitria's proprietary vector (25 µg heavy chain+12.5 µg of each light chain, LC1 and LC2) were mixed in 1.5 mL Eppendorf tube, 1 mL of CHO SFM medium containing 25 µL of 3 mg/mL PEI pH7.0 was added, incubated at RT for 20 min. The mixture of DNA-PEI was loaded into 49 mL of FreeStyle™ CHO-S cells at $1-2 \times 10^6$ cells/mL in 125 mL shaking flask. Cells were shaken for 6 more days. The supernatant was harvested by centrifuging cells at 3,000 rpm for 15 min. The harvested supernatant was purified by Protein A resin. Electrophoresis was performed under reducing conditions and non-reducing conditions employing Gel Biorad Stain-Free 4-15% gels and the corresponding running buffer. Samples were prepared by combining the purified BiXAb® antibodies with 2×SDS sample buffer and heating for 5 min at 95° C. Preparation of reduced samples included the addition of NuPAGE reducing agent prior to heating. The apparent MW was determined using Ladder Precision Plus Protein Unstained Standards (Biorad). FIG. 2 presents the SDS-PAGE pattern of CD38/PD-L1 antibodies under reducing conditions. Two bands corresponding to the composite heavy chain and two co-migrating light chains are observed and are of the expected molecular weight. FIG. 3 presents the SDS-PAGE pattern of CD38/PD-L1 antibodies under non-reducing conditions.

The dominant band at 250 kDa corresponds to the complete CD38/PD-L1 BiXAb® molecule as expected.

Figure 4:
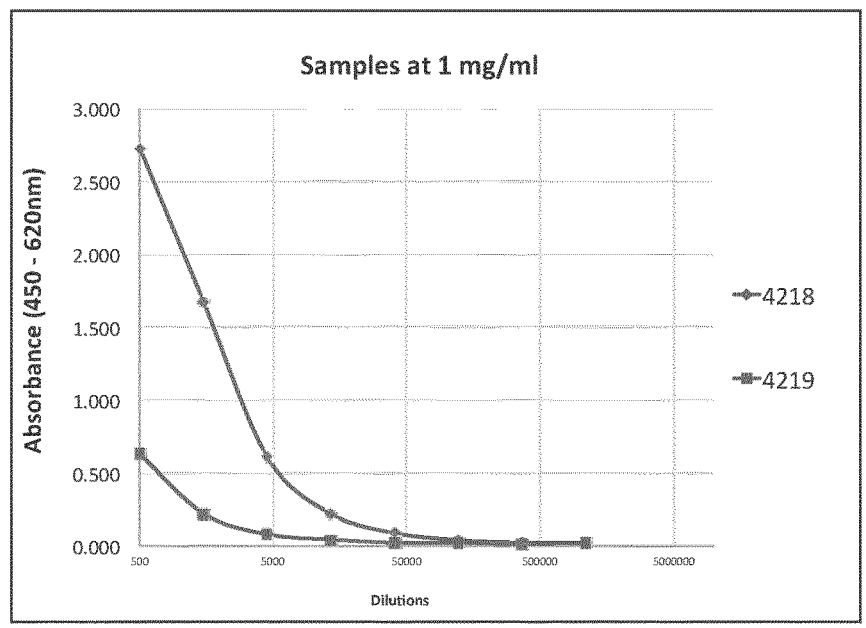
FIG. 4 shows the ELISA binding assay for BiXAbs 4218 and 4219.

For Dual Antigen Binding Plate ELISA Assay the following reagents were used: Recombinant human CD38, Fc-tagged (Creative BioMart); biotinylated Human PD-L1, Avi Tag (AcroBiosystems); Streptavidin-HRP, (Biotechne RD-Systems). Human CD38-Fc fusion protein was coated with 100 µL/well at 2 µg/mL in 1×PBS pH7.4 in Maxisorp plates at 4° C. overnight. The plates were washed 5 times with 1×PBS containing 0.05% Tween-20 (1×PBST), then blocked with 3% non-fat milk/1×PBST at 200 µL/well with shaking at RT for 1 hr. 100 µL/well of BiXAb® 4218 and BiXAb® 4219 at 1 mg/ml stock solution starting at 1/500 dilution in 1×PBS at 1:3 series dilutions were added. The plates were incubated at RT for 1 hr with shaking, followed by 5 washes with 1×PBST. 100 µL/well of 1 µg/mL Biotin-human PD-L1 protein in 1×PBS was added and plates were shaken at RT for 1 hr. After 5 washes with 1×PBST, 100 µL/well of 0.1 µg/mL of Streptavidin-conjugated HRP in 1×PBS was added. The plates were shaken at RT for 1 hr followed by 5 washes with 1×PBST. 100 µL/well TMB substrate in 1×PBS was added for color development. The data were collected at 405 nm for 0.1 sec per well on a Victor II multifunction plate reader. FIG. 4 demonstrates the dual antigen binding profiles of two CD38/PD-L1 BiXAbs®. This profile confirms that both types of binding domains of these molecules (anti-CD38 domains and anti-PD-L1 domains) bind their cognate antigen targets.

Example 2. Preparation of Bispecific Antibody of the Invention BiXAb-6567

Gene Synthesis

The amino acid sequences of anti-CD38 (daratumumab) and anti-PDL1 (atezolizumab) were used to design the DNA sequences, after codon optimization for mammalian expression, using the GeneScript program. These antibodies are referred to as the "parental" anti-CD38 and the "parental" anti-PD-L1 mAbs.

The DNA construct of the heavy chain was designed as such: signal peptide (SEQ ID NO:21), followed by sequence SEQ ID NO:10 [consisting of the variable region, followed by the constant CH1 domain of Fab1 (anti-CD38), in which mutations Leu to Gln and Ser to Val at Kabat positions 124 and 188 were introduced, respectively, followed by the linker, followed by the variable region, followed by the constant CH1 domain of Fab2 (anti-PD-L1), in which mutation Thr to Asp at Kabat position 192 was introduced]; flanking sequences for restriction enzyme digestion were introduced on both ends of the heavy chain DNA construct. The DNA construct for the light chain was designed as such: signal peptide (SEQ ID NO:21), followed by the variable region, followed by the constant Kappa region. For the anti-CD38 light chain, mutations where introduced at Kabat positions 143 (Leu to Gln) and 188 (Ser to Val) in the constant Kappa domain. For the anti-PDL1 light chain, mutations at Kabat positions 133 (Val to Thr) and 176 (Ser to Val) were introduced into the constant Kappa domain. All DNA constructs were synthesized by Gene Art.

PCR reactions, using PfuTurbo Hot Start, were carried out to amplify the inserts, which were then digested with NotI and ApaI, and NotI and HindIII for heavy and light chains, respectively. The double digested heavy chain fragments were ligated with NotI and ApaI treated pcDNA3.1 expression vector (Invitrogen) into which the human IgG1 hinge followed by the CH2-CH3 domains were already inserted. The double-digested light chain fragments were ligated with NotI and HindIII treated pcDNA3.1 expression vector (Invitrogen). Plasmid DNAs were verified by double strand DNA sequencing.

Expression and Purification

The bispecific antibody BiXAb-6567 was produced employing transient gene expression by co-transfecting 3 genes coded on separate vectors in a 2:1:1=HC:LC1:LC2 molecular ratio (1 continuous heavy chain (HC) and 2 light chains (LC)) in CHO-S cells adapted to serum-free medium in suspension (CHO SFM-II medium, Life Technologies™). Typically, for 50 mL scale expression, a total of 50 µg of plasmid DNA (25 µg heavy chain, 12.5 µg of anti-CD38 light chain and 12.5 µg of anti-PD-L1 light chain) were mixed in a 1.5 mL Eppendorf tube, then 1 mL of CHO SFM medium containing 25 µL of 3 mg/mL PEI transfection reagent pH7.0 (Polyplus) was added, and the reaction incubated at room temperature for 20 min. The DNA-PEI mixture was subsequently added to 49 mL of Life Technologies' Invitrogen FreeStyle™ CHO-S cells at 1~2×10⁶/mL in a 125 mL shake flask. Cells were shaken for 6 days. The supernatant was harvested by centrifugation at 3,000 rpm for 15 min. The expression titer of BiXAb-6567 in the supernatant was determined using ForteBio's protein A biosensors (Octet® Systems). BiXAb-6567 was then purified on protein A affinity resin (MabSelect SuRe, GE Healthcare Life Sciences). The antibody was eluted from protein A using 0.1 M glycine pH 3.5, and the eluate was neutralized by 1 M TRIS. The purified antibody, in Dulbecco's PBS (Lonza), was sterile-filtered (0.2 µM sterile filters, Techno Plastic Products AG), and the final concentration determined by reading the optical density (OD) at 280 nm (Eppendorf BioSpectrometer®).

BiXAab-6567 typically exhibited good expression titer (>180 mg/liter) in transient CHO expression. This level of expression is comparable to the level of expression seen with conventional monoclonal antibodies.

SDS Polyacrylamide Gel Electrophoresis

In order to evaluate the quality of purified BiXAb-6567, we performed SDS-PAGE (Experion™ automated electrophoresis system, BioRad). In the presence of sodium dodecyl sulfate (SDS) in the running buffer, the rate at which an antibody migrates in the gel depends primarily on its size, enabling molecular weight determination. This assay was performed under non-reducing conditions and under reducing conditions; the latter permits disruption of the disulfide bonds, and hence visualization of individual polypeptide chains (the light chains and the heavy chain).

Figure 5:
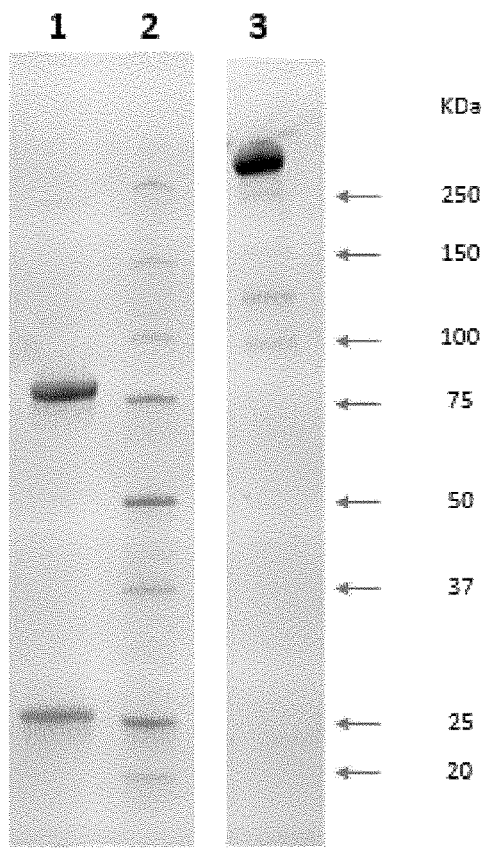
FIG. 5 shows the SDS polyacrylamide gel electrophoresis of BiXAb-6567 under reducing and non-reducing conditions. Lane 1: the migration of BiXAb-6567 under reducing conditions; lane 2: molecular weight markers with the weight of each band indicated; lane 3: the migration of BiXAb-6567 under non-reducing conditions.

The SDS-PAGE data are presented in FIG. 5. Under non-reducing conditions, the quaternary structure of the antibody is maintained, and the molecular weight observed should represent the sum of the molecular weights of the different heavy and light chains. The bispecific antibody of the invention (BiXAb-6567) consists of six chains: two heavy chains and four light chains. The theoretical molecular weight of BiXab-6567 is 244.40 kDa, not accounting for post-translational modifications (PTM), e.g. N-glycosylation in the Fc at asparagine 297. The gel was calibrated using a mixture of standards of known molecular weight. The non-reducing data exhibit a major band running close to the 250 kDa molecular weight standard, which is in accordance with the calculated molecular weight and the expected glycosylation of two asparagines at position 297 in the Fc domain. Under reducing conditions, dithiothreitol (DTT) further denatures BiXAb-6567 by reducing the disulfide linkages and breaking the quaternary structure, and thus the six polypeptide chains should migrate separately in the gel according to their molecular weight. The two identical heavy chains of BiXAb-6567 co-migrate as a single band, and the two pairs of light chains, due to their nearly identical molecular weight, co-migrated as the second band. Therefore, the data exhibit two major bands, at approximately 75 kDa and 25 kDa, based on the mobility of the molecular weight standards. Each heavy chain possessed one N-glycosylation site at asparagine 297, which explains the broadness of the higher molecular weight band and the observed molecular weight slightly higher than calculated (75.44 kDa); this broadening is typical for glycosylated proteins. The calculated molecular weights of the light chains of anti-CD38 (23.40 kDa) and anti-PD-L1 (23.36 kDa) are very similar, and thus resulted in their co-migration.

In conclusion, the SDS-PAGE of BiXAb-6567 exhibited the expected profiles, under both non-reducing and reducing conditions, and was in agreement with the calculated theoretical molecular weights, when accounting for the existence of an N-glycosylation site in the heavy chain.

Size Exclusion Chromatography Analysis

Protein aggregation is frequently observed in engineered protein molecules. We performed analytical size exclusion chromatography (SEC) to assay the high molecular weight species content of the single-step affinity-purified BiXAb-6567 preparation (see Expression and Purification of variants). We employed an SEC-s3000 (300×7.8 mm) column (BioSep) and an Aktapurifier 10 system (GE Healthcare); the assay was conducted at a flow rate of 1 mL/min using PBS buffer pH 7.4.

Figure 6:
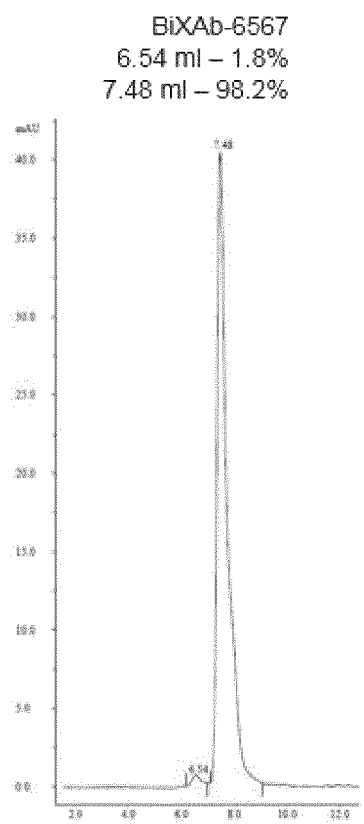
FIG. 6 shows the Size Exclusion chromatography analysis of BiXAb-6567.

The SEC chromatogram presented in FIG. 6 demonstrated that the main peak corresponded to the expected size of the monomeric BiXAb-6567; this peak represented 98.2% of the total sample. In addition, a small peak corresponding to higher molecular weight species (possibly dimers) was observed; this peak represented 1.8% of the total sample. Thus, we concluded that the percentage content of higher molecular weight species is minor, and is similar to conventional monoclonal antibodies produced in CHO expression systems. The narrow and symmetric shape of the monomeric peak suggested that BiXAb-6567 was correctly assembled and was represented by a single species.

Example 3. Characterization of BiXAb-6567 by Differential Scanning Calorimetry

Differential Scanning calorimetry (DSC) was used to compare the thermal stability of BiXAb-6567, the parental anti-CD38 mAb, and the parental anti-PD-L1 mAb. A Microcal™ VP-Capillary DSC system (Malvern Instruments) was used to perform differential scanning calorimetry experiments.

All samples were centrifuged (20,000×g, 5 min, 4° C.), and their protein content was quantitated prior to the DSC analysis using a Nanodrop ND-1000 spectrophotometer (Thermo Scientific) employing the IgG analysis program. For assay, all samples were diluted in PBS to a final concentration of 1 mg/mL.

The pre-equilibration time was 3 min, and the resulting thermograms were acquired between 20 and 110° C. at a scan rate of 60° C./h, a filtering period of 25 sec, and medium feedback. Prior to sample analysis, 5 buffer/buffer scans were measured to stabilize the instrument, and a buffer/buffer scan was performed between each protein/buffer scan. The data were fit to a non-2-state unfolding model, with the pre- and post-transition adjusted by subtraction of the baseline.

Figure 7:
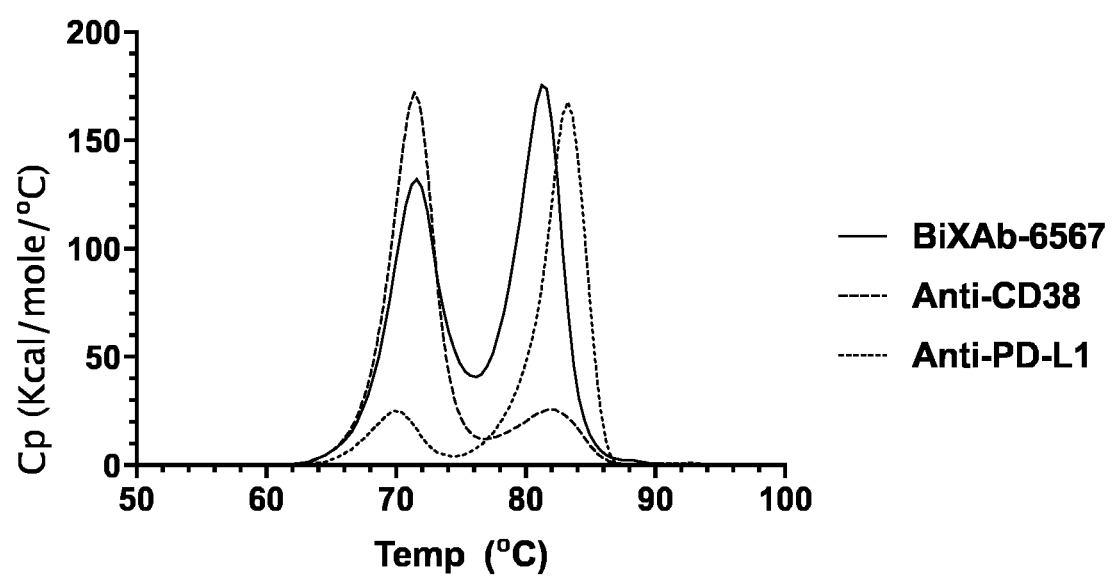
FIG. 7 shows the melting profiles of the two parental antibodies (anti-CD38 and anti-PD-L1) and BiXAb-6567 as determined by Digital Scanning calorimetry.

The DSC curves presented in FIG. 7 (covering the 50 to 100° C. range) demonstrated the manner in which individual Fv regions can lead to different Fab unfolding profiles; this experiment also demonstrated that the Fv regions dictate the apparent stabilities of the Fabs. The DSC profile of the anti-CD38 mAb exhibited two transitions: a large peak having a Cp max of 170 Kcal/mole/° C. and a Tm1 of 70.9° C., corresponding to the unfolding of both CH2 and Fab domains, and a small peak having a Cp max of 20 Kcal/mole/° C. and a Tm2 of 81.5° C., corresponding to the unfolding of the CH3 domain. The DSC profile of the anti-PD-L1 mAb exhibited two transitions: a small peak having a Cp max of 20 Kcal/mole/° C. and a Tm1 of 69.9° C., corresponding to the unfolding of the CH2 domain, and a large peak having a Cp max of 160 Kcal/mole/° C. and a Tm2 of 83.4° C., corresponding to the unfolding of both CH3 and Fab domains.

The DSC profile of BiXAb-6567 also exhibited two transitions with two large peaks. The first peak had a Cp max of 130 Kcal/mole/° C. and a Tm1 of 71.5° C., and corresponded to the unfolding of the CH2 and Fab domains of the anti-CD38 mAb; the second peak had a Cp max of 170 Kcal/mole/° C. and a Tm2 of 81.5° C., and corresponded to the unfolding of the CH3 and Fab domains of the anti-PD-L1 mAb. Thus, the DSC profile of BiXAb-6567 resembled the superposition of the two DSC profiles of the two parental mAbs, and illustrated the excellent assembly and stability of BiXAb-6567. The Tonset of BiXAb-6567 (63.3° C.) was similar to that of the parental mAbs (anti-CD38 Tonset=63.5° C. and anti-PD-L1 Tonset=63.2° C.), indicating that BiXAb-6567 possessed stability properties similar to those of the parental antibodies. The calculated ΔH of BiXAb-6567 was 1560 kcal/mole, reflecting the larger size of the bispecific molecule relative to the two parental antibodies (anti-CD38 ΔH=963 kcal/mole and anti-PD-L1 ΔH=820 kcal/mole).

Definitions

Tm or denaturation/melting temperature is the point at which the concentration of the unfolded and folded species is equal, and is the midpoint of the unfolding transition. As a parameter, it describes the susceptibility of the protein to thermal denaturation, and thus it relates to the stability of the protein. The higher the Tm the more stable the protein.

Tonset is the temperature at which the unfolding transition begins. The values for this parameter are usually 5 to 10° C. lower than the Tm. It is also a parameter describing protein stability, but with relevance to the resistance to thermal denaturation.

ΔH is the calorimetric enthalpy of unfolding, and reflects the disruption of intramolecular interactions in the protein (i.e. breaking of intra- and inter-domain interactions). The thermal unfolding process is endothermic, and thus yields positive enthalpy values. The calorimetric enthalpy (ΔH) is the area under the thermal unfolding transition peak.

Example 4. Cell Free Binding Properties of BiXAb-6567

Direct CD38 Antigen-Binding Plate ELISA Assay

100 µl of either parental mAb, anti-CD38 or anti-PDL1, each at a concentration of 3 µg/mL, prepared by dilution with PBS pH 7.4, were used to coat Maxisorp plates at 4° C. overnight. Also, BiXAb-6567, at a concentration of 5 µg/mL, prepared by dilution with PBS pH 7.4, was used to coat Maxisorp plates at 4° C. overnight. The plates were washed 5 times with 1×PBS containing 0.05% Tween-20 (PBST), and then blocked with 200 μL/well 1% BSA in 1×PBS at room temperature for 2 hrs. The plates were subsequently washed 5 times with 1×PBST. A seven-point 3-fold dilution series of recombinant CD38 His/Flag-tagged (Creative Biomart) in 1×PBS, starting at 1 μg/mL, was prepared; 100 μL of each dilution step was added per assay well. The plates were incubated at room temperature for 1 hr, and washed 5 times with 1×PBST. 100 μL/well of anti-Flag-tag antibody-conjugated HRP (Abcam), diluted 10,000-fold in 1×PBS, was added and the plates were incubated at room temperature for 1 hr. After 5 washes with 1×PBST, 100 μL/well of TMB substrate in 1×PBS was added for colorimetric readout, and the plates incubated for 15 min at room temperature for color development. The assay data were collected employing a Victor2 microplate reader (Perkin Elmer) at 650 nm. BiXAb-6567 exhibited a dose-dependent binding curve very similar to that of the parental anti-CD38 antibody (FIG. 8A). The EC50 of CD38 binding for both antibodies were as follows: EC50[BiXAb-6567]=171 ng/mL and EC50[anti-CD38]=199 ng/mL. This result suggested that BiXAb-6567 possessed correctly assembled anti-CD38 Fab domains, since it exhibited binding similar to that of the parental anti-CD38 mAb. The parental anti-PDL1 mAb, used as a negative control, did not exhibit any binding, as expected.

Direct PDL1 Antigen Binding Plate ELISA Assay.

100 μL of biotinylated human PD-L1 protein (AcroBiosystems) at a concentration of 1 μg/mL, prepared by dilution with 1×PBS pH7.4, was used to coat Maxisorp plates at 4° C. overnight. The plates were washed 5 times with PBST, and then blocked with 200 μL/well 1% BSA in 1×PBS at room temperature for 2 hrs. The plates were subsequently washed 5 times with 1×PBST. Seven-point 3-fold dilution series of either the anti-CD38 mAb (starting at 0.3 mg/mL), or the anti-PD-L1 mAb (starting at 0.3 mg/mL), or BiXAb-6567 (starting at 0.5 mg/mL) in 1×PBS were prepared; 100 μL of each dilution step was added per assay well. The plates were incubated at room temperature for 1 hr and washed 5 times with 1×PBST. 100 μL/well of anti-human antibody (IgG H&L)-conjugated HRP (Abliance), diluted 5,000-fold in 1×PBS, was added, and the plates were incubated at room temperature for 1 hr. After 5 washes with 1×PBST, 100 μL/well of TMB substrate in 1×PBS was added for colorimetric readout, and the plates incubated for 15 min at room temperature for color development. The assay data were collected employing a Victor2 microplate reader (Perkin Elmer) at 650 nm.

BiXAb-6567 exhibited a dose-dependent binding curve very similar to that of the parental anti-PD-L1 antibody (FIG. 8B). The EC50 of PD-L1 binding for both antibodies were as follows: EC50[BiXAb-6567]=93 ng/mL and EC50 [anti-PD-L1]=72 ng/mL. This result suggested that BiXAb-6567 possessed correctly assembled anti-PD-L1 Fab domains, since it exhibited binding similar to that of the parental anti-PD-L1 mAb. The parental anti-CD38 mAb, used as a negative control, did not exhibit any binding, as expected.

Dual Antigen-Binding ELISA Assay

100 μL of recombinant human Fc-tagged CD38 (Creative BioMart), at 2 μg/mL prepared by dilution with 1×PBS pH7.4, was used to coat Maxisorp plates at 4° C. overnight. The plates were washed 5 times with 1×PBST, and then blocked with 200 μL/well 1% BSA in 1×PBS at room temperature for 2 hrs. The plates were washed 5 times with 1×PBST. A seven-point three-fold dilution series in 1×PBS of BiXAb-6567 (starting at 1 μg/mL) was prepared, and 100 μL of each dilution step was added per assay well. The plates were incubated at room temperature for 1 hr, and subsequently washed 5 times with 1×PBST. 100 μL/well of 1 μg/mL biotinylated human PD-L1 (AcroBiosystems) in 1×PBS was added, and the plates were incubated at room temperature for 1 hr. After 5 washes with 1×PBST, 100 μL/well of 0.1 μg/mL of streptavidin-conjugated HRP (Biotechne) prepared by dilution with 1×PBS was added. The plates were incubated at room temperature for 1 hr. After 5 washes with 1×PBST, 100 μL/well of TMB substrate in 1×PBS was added for colorimetric readout, and the plates incubated for 15 min at room temperature for color development. The assay data were collected employing a Victor2 microplate reader (Perkin Elmer) at 650 nm.

BiXAb-6567 exhibited a dose-dependent binding curve in the dual ELISA format, suggesting that it possessed correctly assembled anti-CD38 and anti-PD-L1 Fab domains (FIG. 8C). This demonstrated that BiXAb-6567 is a bispecific antibody capable of binding CD38 and PD-L1 simultaneously with EC50=144 ng/mL. Neither of the two parental mAbs, anti-CD38 or anti-PDL1, exhibited any binding in this dual ELISA format, as expected.

Example 5. Determination of Relative Binding Activity by Fluorescence-Activated Cell Sorting (FACS)

CHO-CD38 cells (CHO cells stably transfected with full length human CD38) were cultured in DMEM-Glutamax-I medium supplemented with 100 μg/ml penicillin, 100 μg/ml streptomycin, 10% fetal calf serum and 500 μg/ml geneticin. SKOV-3 cells and RPMI-8226 cells were cultured in RPMI 1640-Glutamax-I medium, supplemented with 100 μg/ml penicillin, 100 μg/ml streptomycin, and 10% fetal calf serum.

3×105 cells (CHO-CD38, or SKOV-3, or RPMI-8226) per each sample were used. Cells were washed 1× with the PBA solution (PBS supplemented with 1% BSA and 0.05% Na-azide). For the determination of the FACS profiles, the cells were stained with the respective antibodies at a concentration of 50 μg/ml in a volume of 30 μl. For the titration of BiXAb-6567 and the parental anti-CD38 antibody, and subsequent determination of the binding parameters, CHO-CD38 cells were stained with the respective antibodies at the indicated concentrations in a volume of 30 μl. Cells were incubated for 30 min on ice and then washed 2 times with 1 ml of PBA solution. Cells were incubated with fluorescently labelled anti-human kappa or anti-human IgG Fc gamma specific secondary antibodies on ice in the dark for 30 min, and then washed 2 times with 1 ml PBA solution; lastly, cells were re-suspended in a final volume of 500 μl PBA solution. Samples were assayed using either an Epics-XL or a Navios flow cytometer (Beckman Coulter). 10.000 events were acquired in each experiment.

The binding profiles of BiXAb-6567 and the parental anti-CD38 and anti-PD-L1 parental antibodies are presented in FIGS. 9A-C. We chose to test a multiple myeloma cell line, RPMI-8226, which expresses high levels of CD38 and negligible levels of PD-L1 (FIG. 9A); a CHO-CD38 cell line that expressed a very high level of CD38 due to stably transfected full length CD38 (FIG. 9B); and an ovarian cancer cell line SKOV-3, which is known to express PD-L1 (FIG. 9C). These profiles exhibited a single peak for BiXAb-6567 that was very similar to the profiles of both parental antibodies on the 3 cell lines. This suggested that BiXAb-6567 is correctly folded and possesses binding attributes similar to those of the parental antibodies. As expected, CHO-CD38 expressed only CD38 and no PD-L1, whereas SKOV-3 expressed only PD-L1 and no CD38.

In order to quantitatively confirm that the binding properties of BiXAb-6567 are similar to those of the parental anti-CD38 antibody, a titration of BiXAb-6567 and the anti-CD38 parental antibody was performed employing CHO-CD38 cells, as presented in FIG. 10. The EC50 of BiXAb-6567 was determined to be 17.1 nM and that of the parental anti-CD38 was 8.5 nM, confirming the similar binding properties of the anti-CD38 Fab domains in BiXAb-6567 and in the parental anti-CD38 antibody. Negative controls in this experiment, anti-PD-L1 and anti-CD20 antibodies, demonstrated no binding to CHO-CD38 cells, as expected.

Example 6. Antibody Dependent Cell-Mediated Cytotoxicity (ADCC) with Unfractionated Non-Preactivated Mononuclear Cells (MNC)

CHO-CD38, SKOV-3, and RPMI-8226 cells were cultured as described in Example 5 above.

For preparation of MNC the following procedure was employed. Freshly drawn peripheral blood was anti-coagulated with citrate. Subsequently, 5 ml of Ficoll-Paque PLUS solution was layered with 6 ml anti-coagulated whole blood. Samples were centrifuged for 20 min at 2,500 rpm at RT with no subsequent centrifuge breaking. MNC were collected from the plasma/Ficoll interface. The MNC cell suspension was diluted 1:10 in PBS and centrifuged for 5 minutes at 1,800 rpm at room temperature. The supernatant was removed, and the erythrocytes were lysed by addition of 45 ml ice-cold distilled water to the cell suspension for 30 seconds, after which 5 ml of 10×PBS was added. The cells were centrifuged for 5 min at 1800 rpm at room temperature and washed with 1×PBS three times to remove platelets. Finally cells were re-suspend in 5 ml cell culture medium. Cell numbers were adjusted to achieve 40:1=Effector cell:Tumor cell ratio in the ADCC assays.

For the ADCC $^{51}$Chromium release assay, $1\times10^6$ target cells (RPMI 8226, SKOV-3, or CHO-CD38) were incubated with 100 µCi 51Chromium in 200 µl PBS for 2 hours at 37° C. and 5% CO2. After 2 hours incubation, cells were washed three times with 7 ml of medium and finally re-suspended at a concentration of $0.1\times10^6$ cells/ml. Target cells (5,000 cells/well) and MNC in the presence of antibodies were incubated in a 96-well micro-titer plate (200 µl assay volume) for 3 hours at 37° C. and 5% CO2. For the determination of maximal target cell lysis (=maximal cpm) Triton X-100 was added. To determine basal $^{51}$Chromium release (=basal cpm) target cells were not further manipulated. After 4 hr incubation, micro-titer plates were centrifuged for 5 min at 2000 rpm and 25 µl supernatant was mixed with 125 µl of Optiphase Supermix (Perkin Elmer) and incubated in a shake incubator for 1 min. Samples were assayed in a MicroBeta TriLux (Perkin Elmer) beta-counter instrument. Target cell lysis was calculated using the following formula:

% lysis=(experimental cpm−basal cpm)/(maximal cpm−basal cpm)×100.

All of the measurements were performed in triplicate.

ADCC assays of CD38+ cells (RPMI-8226 and CHO-CD38) were performed employing non-pre-activated MNC as effector cells (FIGS. 11 and 12) The assays showed potent cytotoxicity of BiXAb-6567 and the anti-CD38 antibody on RPMI-8226 cells with EC50 of 0.8 nM and 0.3 nM, respectively; on CHO-CD38 cells, the cytotoxicity of BiXAb-6567 and the anti-CD38 antibody had EC50 of 0.2 nM and 0.07 nM, respectively. Anti-PD-L1 showed minimal activity on both cells lines; two negative control mAbs, anti-CD20 and anti-HER2, did not facilitate any lysis, as expected. These results demonstrate the potent ADCC activity of BMX-6567 against CD38+ cells, which is similar to that of the parental anti-CD38 antibody.

Example 7. ADCC with Enriched Pre-Activated NK Cells

SKOV3 cells, RPMI 8226, and CHO-CD38 cells were cultured as described in Example 5. MNC were prepared as described in Example 6. NK cells were isolated from MNC by negative selection employing the "NK cell isolation kit, human" (Miltenyi) according to the manufacturer's instructions. NK cells were cultivated over night at a seeding density of $2\times10^6$ cells/ml in RPMI medium supplemented with 10% fetal calf serum. IL-12 or IL-15 was added to a final concentration of 10 ng/ml. ADCC assays were performed as outlined in Example 5 with the exception that the Effector cell:Tumor cell ratio was kept at 10:1 and the duration of the reaction was reduced to 3 hr.

The ADCC properties of the anti-PD-L1 moiety of the BiXAb-6567 were assayed on the PD-L1+ cell line SKOV-3 employing either IL-12 or IL-15 pre-activated enriched NK cells. The results are presented in FIGS. 13 and 14. This experiment compared the ADCC properties of BiXAb-6567 with those of the parental anti-PD-L1 antibody; as a positive control an anti-HER2 antibody was employed, and as negative controls an anti-CD20 antibody and the parental anti-CD38 antibody were employed since SKOV-3 cells are PD-L1+/HER2+/CD20−/CD38−. FIGS. 13 and 14 demonstrate the potent ADCC activity of BiXAb-6567 and the parental anti-PD-L1 antibodies, independently of whether IL-12 or IL-15 was employed in culturing the NK cells. The EC50 of BiXAb-6567 and the parental anti-PD-L1 antibodies were 0.007 nM and 0.03 nM, respectively, when IL-12 was used. The profiles were even more similar when IL-15 was employed; however the curve fits did not converge, thus preventing the calculation of EC50 values. These results demonstrate the potent ADCC activity of BMX-6567 against PD-L1+ cells, which is similar to that of the parental anti-PD-L1 antibody.

The invention claimed is:

1. A bispecific molecule comprising at least one anti-CD38 domain and at least one anti-PD-L1 domain, which are capable of simultaneous binding to CD38 and PD-L1 antigens, respectively, wherein the bispecific molecule is a full length antibody comprising two heavy chains and four light chains, wherein each heavy chain comprises
a) a Fc region comprising Hinge-CH2-CH3 domains,
b) which Fc region is linked to Fab heavy chain (CH1-VH) of atezolizumab,
c) which in turn is linked to Fab heavy chain (CH1-VH) of daratumumab, by a hinge-derived polypeptide linker sequence, wherein said polypeptide linker sequence links the N-terminus of Fab heavy chain VH domain of atezolizumab with the C-terminus of CH1 domain of daratumumab, wherein the Fc region comprises a Hinge domain of SEQ ID NO: 26, a CH2 domain of SEQ ID NO: 27 and a CH3 domain of SEQ ID NO: 28; wherein the Fab heavy chain of atezolizumab comprises a VH domain of SEQ ID NO: 24 and a CH1 domain of SEQ ID NO: 25; and wherein the Fab heavy chain of daratumumab comprises a VH domain of SEQ ID NO: 22 and a CH1 domain of SEQ ID NO: 23;

and wherein two light chains comprise SEQ ID NO: 11 and two other light chains comprise SEQ ID NO: 12.

2. The bispecific molecule of claim 1, said bispecific molecule comprising a) two heavy chains, each comprising SEQ ID NO: 10 and b) four light chains, two comprising SEQ ID NO: 11 and the other two comprising SEQ ID NO: 12.

3. A method for producing a bispecific molecule, said method comprising the following steps:
   a) culturing in suitable medium and culture conditions a host cell expressing an antibody heavy chain and antibody light chains according to claim 1, and
   b) recovering said bispecific molecules from the culture medium or from said cultured cells.

4. A method of treating cancer comprising administering a bispecific molecule according to claim 1 to a subject having cancer.

5. The method according to claim 4, wherein said cancer is multiple myeloma, lymphoma or leukemia.

6. The bispecific molecule of claim 1, wherein the polypeptide linker sequence comprises the amino acid sequence:
   EPKX1CDKX2HX3X4PPX5PAPELLGGPX6X7PPX8PX9PX10GG (SEQ ID NO: 13),
   wherein X1, X2, X3, X4, X5, X6, X7, X8, X9, and X10, identical or different, are any amino acid.

7. The bispecific molecule of claim 1, wherein the polypeptide linker sequence comprises SEQ ID NO: 15.

* * * * *

UNITED STATES PATENT AND TRADEMARK OFFICE
CERTIFICATE OF CORRECTION

PATENT NO. : 11,505,616 B2
APPLICATION NO. : 16/088181
DATED : November 22, 2022
INVENTOR(S) : Eugene Zhukovsky, Olivier Leger and Richard J. Morse Page 1 of 1

It is certified that error appears in the above-identified patent and that said Letters Patent is hereby corrected as shown below:

In the Specification

Column 4,
Line 65, "chains: A and K" should read --chains: $\lambda$ and $\kappa$--.

Signed and Sealed this
Fifth Day of September, 2023

Katherine Kelly Vidal
*Director of the United States Patent and Trademark Office*